(12) United States Patent
Meier et al.

(10) Patent No.: US 7,947,831 B2
(45) Date of Patent: *May 24, 2011

(54) SULFOXIDES OR SULFONES GRAFTED ONTO POLYMERS

(75) Inventors: Hans-Rudolf Meier, Basel (CH); Gerrit Knobloch, Magden (CH); Pierre Rota-Graziosi, Mulhouse (FR); Samuel Evans, Marly (CH); Paul Dubs, Cham (CH); Michèle Gerster, Birsfelden (CH)

(73) Assignee: BASF SE Ludwigshafen (DE)

( * ) Notice: Subject to any disclaimer, the term of this patent is extended or adjusted under 35 U.S.C. 154(b) by 990 days.

This patent is subject to a terminal disclaimer.

(21) Appl. No.: 11/523,441

(22) Filed: Sep. 19, 2006

(65) Prior Publication Data

US 2007/0015870 A1    Jan. 18, 2007

Related U.S. Application Data

(62) Division of application No. 10/473,848, filed as application No. PCT/EP02/03381 on Mar. 26, 2002, now Pat. No. 7,160,955.

(30) Foreign Application Priority Data

Apr. 6, 2001 (CH) .................................. 0659/01

(51) Int. Cl.
C07C 317/00 (2006.01)
C07C 317/04 (2006.01)
C07C 317/06 (2006.01)
C07C 317/10 (2006.01)
C07C 317/18 (2006.01)
C07C 317/44 (2006.01)

(52) U.S. Cl. ............ 544/180; 548/255; 560/55; 568/27; 568/28; 568/30; 568/31; 568/32; 568/34; 568/36; 568/37

(58) Field of Classification Search .............. 560/55; 568/27, 28, 30, 31, 32, 34, 36, 37; 544/180; 548/255

See application file for complete search history.

(56) References Cited

U.S. PATENT DOCUMENTS

| 4,021,468 A | 5/1977 | Lind | 260/470 |
| 4,287,320 A | 9/1981 | Kolb | 525/340 |
| 5,258,433 A | 11/1993 | Meier et al. | 524/155 |
| 6,797,755 B1 | 9/2004 | Meier et al. | 524/155 |

FOREIGN PATENT DOCUMENTS

| EP | 0473549 | 3/1992 |
| GB | 922367 | 3/1963 |
| GB | 1135699 | 12/1968 |
| WO | 97/14678 | 4/1997 |
| WO | 01/29126 | 4/2001 |

OTHER PUBLICATIONS

Derzhinskii et al. ,CAPLUS AN 1980:132241, abstracting SU 722905, Mar. 1980.*
Guan et al. CAPLUS AN 1995:997647, abstracting CN 1105021, Jul. 1995.*
Kader et al. CAPLUS AN 1962:462443 Elimination-addition. II. Quinonoid intermediates in reactions of omega.,.omega.'-dialkylsulfenylxylene (1962).*
STN File Registry for registry No. 90223-89-5, no. author or month of publication(2010).*
CAPLUS AN 1962:462442 Kader, A. T.; Stirling, C. J. M., Elimination-addition. I. Displacement of sulfonyl groups from diarylsulfonylalkanes (1962).*
Michihata et al. , electronic translation of specification of JP 2002-040232, (2002).*
Derwent Abstract 1994-253082 [31] for JP 6184534 (1994).

* cited by examiner

Primary Examiner — Jeffrey C Mullis
(74) Attorney, Agent, or Firm — Tyler A. Stevenson

(57) ABSTRACT

Polymers grafted with a compound of formula I,

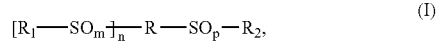

wherein the general symbols are as defined within, have outstanding stability against oxidative, thermal, dynamic, light-induced and/or ozone-induced degradation.

2 Claims, No Drawings

SULFOXIDES OR SULFONES GRAFTED ONTO POLYMERS

This is a divisional of U.S. application Ser. No. 10/473,848, filed Oct. 2, 2003, now U.S. Pat. No. 7,160,955, which is a national stage of international application No. PCT/EP02/03381 filed Mar. 26, 2002.

The present invention relates to sulfoxides or sulfones grafted onto polymers and to compositions comprising such novel grafted polymers and further additives. The present invention relates also to novel sulfoxides and sulfones and to a method of stabilising polymers against oxidative, thermal, dynamic, light-induced and/or ozone-induced degradation using sulfoxides or sulfones and to a method of grafting sulfoxides or sulfones onto polymers.

A customary method of stabilising and modifying polymers and their properties is reactive extrusion. In that method, additives are added to the thermoplastic polymer during extrusion in order to modify the properties of the polymer. That can be accomplished, for example, by grafting an unsaturated compound onto the polymer. Such reactive grafting processes are customarily performed by the combined use of an unsaturated compound and a peroxide as a free-radical-former. When the polymer is modified with functional monomers, for example maleic anhydride, copolymers are obtained that are used as compatibilisers (compatibility promoters) or adhesion promoters.

Current methods have crucial disadvantages, however, which are attributable to the use of peroxides as free-radical-formers. Whilst undesirable subsidiary reactions influence the processing characteristics of the polymers (depending on the type of polymer used there may occur, for example, cross-linking/gel formation or polymer degradation), reaction products of the peroxide and peroxide residues cause a deterioration in the long-term stability of the polymer. Furthermore, considerable safety precautions have to be taken in the case of polymer processing with the addition of peroxides.

WO-A-97/14678 discloses a specific group of N-acylated compounds which may also contain a sulfoxide group. Those compounds are suitable for grafting onto substrates containing free double bonds (page 4, line 15).

The known grafting agents do not in every respect satisfy the high requirements expected of a grafting agent, especially in respect of storage stability, water absorption, sensitivity to hydrolysis, stabilisation during processing, long-term stabilisation, colour characteristics, volatility, migration characteristics, compatibility and light stabilisation. There is therefore still a need for effective grafting agents for polymers that are sensitive to oxidative, thermal, dynamic, light-induced and/or ozone-induced degradation.

It has now been found that a specific group of sulfoxides or sulfones are especially well suited as grafting agents for polymers that are sensitive to oxidative, thermal, dynamic, light-induced and/or ozone-induced degradation.

The present invention accordingly relates to polymers grafted with a compound of formula I

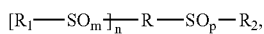

(I)

wherein, when n is 0,
R is $C_1$-$C_{25}$alkyl, $C_2$-$C_{18}$hydroxyalkyl,

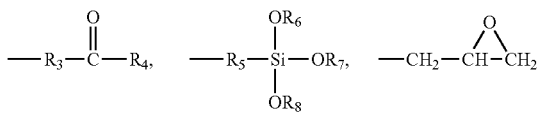

or a radical of formula II, III, IV, V, VI, VII, VIII or IX

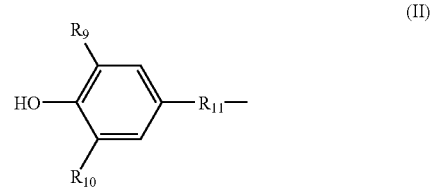

(II)

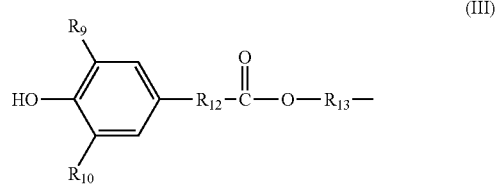

(III)

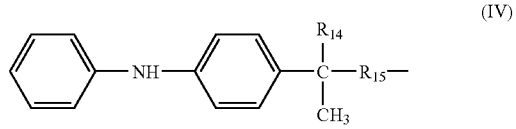

(IV)

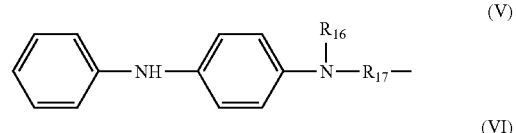

(V)

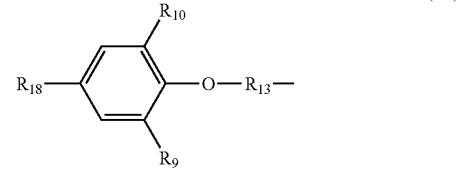

(VI)

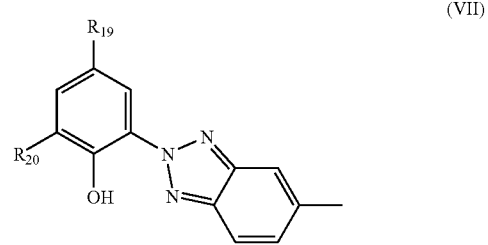

(VII)

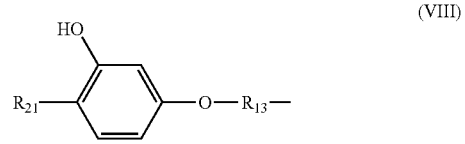

(VIII)

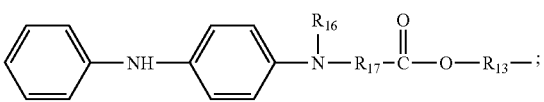

(IX)

when n is 1,
R is $C_1$-$C_{18}$alkylene,

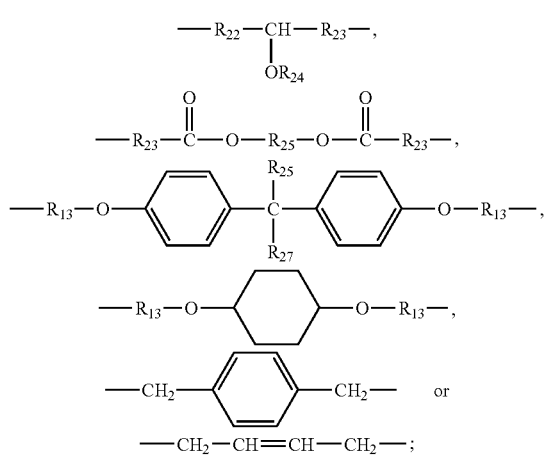

when n is 2,

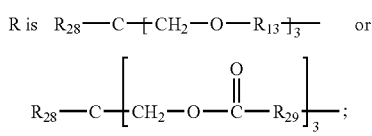

when n is 3,

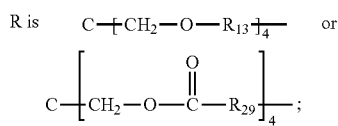

$R_1$ is $C_1$-$C_{25}$alkyl,

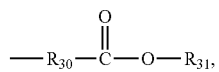 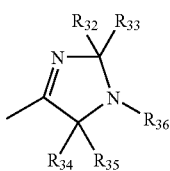

or $C_2$-$C_{18}$hydroxyalkyl,
$R_2$ is $C_1$-$C_{25}$alkyl,

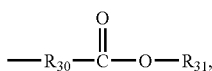 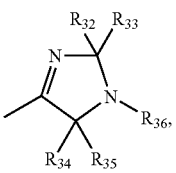

$C_2$-$C_{18}$hydroxyalkyl or a radical of formula III or IX,
$R_3$ is $C_1$-$C_{18}$alkylene, or $C_2$-$C_{18}$alkylene interrupted by oxygen or by sulfur,
$R_4$ is hydroxy, $C_1$-$C_{18}$alkoxy, or $C_3$-$C_{18}$alkoxy interrupted by oxygen or by sulfur,
$R_5$ is $C_1$-$C_{12}$alkylene, or $C_2$-$C_{12}$alkylene interrupted by oxygen, $R_6$, $R_7$ and $R_8$ are each independently of the others hydrogen, $C_1$-$C_{12}$alkyl, $C_2$-$C_{12}$alkyl interrupted by oxygen or by sulfur; or $C_3$-$C_{12}$alkenyl,
$R_9$ is hydrogen, $C_1$-$C_8$alkyl, $C_5$-$C_8$cycloalkyl, $C_7$-$C_9$phenylalkyl or phenyl,
$R_{10}$ is $C_1$-$C_8$alkyl, $C_5$-$C_8$cycloalkyl, $C_7$-$C_9$phenylalkyl, phenyl,

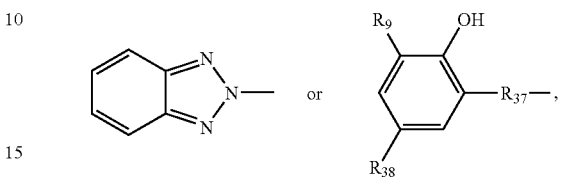

$R_{11}$ is a direct bond or unsubstituted or $C_1$-$C_4$alkyl-substituted $C_1$-$C_8$alkylene,
$R_{12}$ is a direct bond or unsubstituted or $C_1$-$C_4$alkyl-substituted $C_1$-$C_8$alkylene,
$R_{13}$ is $C_1$-$C_8$alkylene or

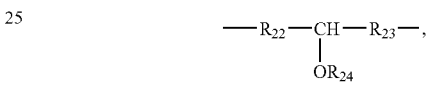

$R_{14}$ is hydrogen or $C_1$-$C_4$alkyl,
$R_{15}$ is $C_1$-$C_4$alkylene,
$R_{16}$ is hydrogen, cyclohexyl or $C_3$-$C_{12}$alkyl,
$R_{17}$ is $C_1$-$C_8$alkylene or

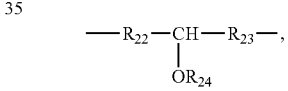

$R_{18}$ is hydrogen, $C_1$-$C_{12}$alkyl or a radical of formula II,
$R_{19}$ is $C_1$-$C_{12}$alkyl or $C_7$-$C_9$phenylalkyl,
$R_{20}$ is $C_1$-$C_{12}$alkyl or $C_7$-$C_9$phenylalkyl,
$R_{21}$ is

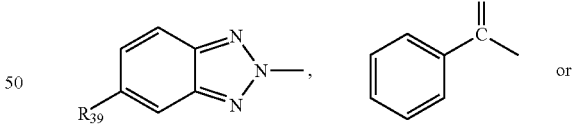

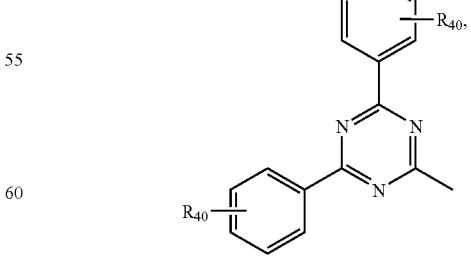

$R_{22}$ is a direct bond or $C_1$-$C_8$alkylene,
$R_{23}$ is $C_1$-$C_8$alkylene,
$R_{24}$ is hydrogen, $C_1$-$C_{25}$alkyl, $C_2$-$C_{25}$alkanoyl,

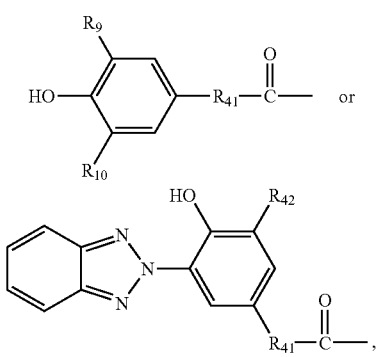

$R_{25}$ is $C_2$-$C_{18}$alkylene or $C_2$-$C_{18}$alkylene interrupted by oxygen or by sulfur, $R_{26}$ and $R_{27}$ are each independently of the other hydrogen, $CF_3$, $C_1$-$C_{12}$alkyl or phenyl, or $R_{26}$ and $R_{27}$, together with the carbon atom to which they are bonded, form a $C_5$-$C_8$cycloalkylidene ring that is unsubstituted or substituted by from 1 to 3 $C_1$-$C_4$alkyl groups, $R_{28}$ is $C_1$-$C_8$alkyl, $R_{29}$ is $C_1$-$C_{12}$alkylene, $R_{30}$ is $C_1$-$C_8$alkylene, $R_{31}$ is $C_1$-$C_{25}$alkyl, $R_{32}$, $R_{33}$, $R_{34}$ and $R_{35}$ are each independently of the others $C_1$-$C_8$alkyl; or the radicals $R_{32}$ and $R_{33}$ or the radicals $R_{34}$ and $R_{35}$, together with the carbon atom to which they are bonded, form a $C_5$-$C_{12}$cycloalkylidene ring, $R_{36}$ is hydrogen, $C_1$-$C_{18}$alkyl, $C_3$-$C_6$alkenyl, $C_3$-$C_6$alkynyl, $C_7$-$C_{12}$phenylalkyl, $C_1$-$C_8$acyl, $C_1$-$C_{18}$alkoxy, $C_1$-$C_{18}$hydroxyalkoxy, $C_2$-$C_{18}$alkenyloxy or $C_5$-$C_{12}$cycloalkoxy, $R_{37}$ is $C_1$-$C_4$alkylene, sulfur or $C_2$-$C_8$alkylidene, $R_{38}$ is hydrogen, $C_1$-$C_8$alkyl, $C_5$-$C_8$cycloalkyl or phenyl, $R_{39}$ is hydrogen, halogen, —SO—$C_1$-$C_{25}$alkyl or —$SO_2$—$C_1$-$C_{25}$alkyl, $R_{40}$ is hydrogen, $C_1$-$C_8$alkyl or phenyl, $R_{41}$ is a direct bond, or unsubstituted or $C_1$-$C_4$alkyl-substituted $C_1$-$C_8$alkylene, $R_{42}$ is hydrogen, $C_1$-$C_8$alkyl, $C_5$-$C_8$cycloalkyl or $C_7$-$C_9$phenylalkyl, m is 0, 1 or 2, n is 0, 1, 2 or 3, and p is 1 or 2.

Alkyl containing up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, isooctyl, 2-ethylhexyl, 1,1,3-trimethylhexyl, 1,1,3,3-tetramethylpentyl, n-nonyl, tert-nonyl, decyl, undecyl, 1-methylundecyl, n-dodecyl, tert-dodecyl, 1,1,3,3,5,5-hexamethylhexyl, tridecyl, tetradecyl, pentadecyl, hexadecyl, heptadecyl, octadecyl or eicosyl.

Hydroxyalkyl containing from 2 to 18 carbon atoms is a branched or unbranched radical containing preferably from 1 to 3, especially 1 or 2, hydroxy groups, for example hydroxyethyl, 3-hydroxypropyl, 2-hydroxypropyl, 4-hydroxybutyl, 3-hydroxybutyl, 2-hydroxybutyl, 5-hydroxypentyl, 4-hydroxypentyl, 3-hydroxypentyl, 2-hydroxypentyl, 6-hydroxyhexyl, 5-hydroxyhexyl, 4-hydroxyhexyl, 3-hydroxyhexyl, 2-hydroxyhexyl, 7-hydroxyheptyl, 6-hydroxyheptyl, 5-hydroxyheptyl, 4-hydroxyheptyl, 3-hydroxyheptyl, 2-hydroxyheptyl, 8-hydroxyoctyl, 7-hydroxyoctyl, 6-hydroxyoctyl, 5-hydroxyoctyl, 4-hydroxyoctyl, 3-hydroxyoctyl, 2-hydroxyoctyl, 9-hydroxynonyl, 10-hydroxydecyl, 11-hydroxyundecyl, 12-hydroxydodecyl, 13-hydroxytridecyl, 14-hydroxytetradecyl, 15-hydroxypentadecyl, 16-hydroxyhexadecyl, 17-hydroxyheptadecyl, 18-hydroxyoctadecyl or 20-hydroxyeicosyl. A preferred meaning of R is $C_2$-$C_{12}$hydroxyalkyl, especially $C_2$-$C_8$hydroxyalkyl, for example hydroxyethyl.

Unsubstituted or $C_1$-$C_4$alkyl-substituted $C_1$-$C_{18}$alkylene containing preferably from 1 to 3, especially 1 or 2, branched or unbranched alkyl group radicals, is a branched or unbranched radical, for example methylene, ethylene, propylene, trimethylene, tetramethylene, pentamethylene, hexamethylene, heptamethylene, octamethylene, decamethylene, dodecamethylene or octadecamethylene.

$C_2$-$C_{18}$Alkylene interrupted by oxygen or by sulfur is, for example, —$CH_2$—O—$CH_2$—, —$CH_2CH_2$—O—$CH_2CH_2$—, —$CH_2$—S—$CH_2$—, —$CH_2CH_2$—S—$CH_2CH_2$—, —$CH_2$—O—$CH_2CH_2$—O—$CH_2$—, —$CH_2CH_2$—O—$CH_2CH_2$—O—$CH_2CH_2$—, —$CH_2$—(O—$CH_2CH_2$—)$_2$O—$CH_2$—, —$CH_2CH_2$—(O—$CH_2CH_2$—)$_2$O—$CH_2CH_2$—, —$CH_2$—(O—$CH_2CH_2$—)$_3$O—$CH_2$—, —$CH_2$—(O—$CH_2CH_2$—)$_4$O—$CH_2$— or —$CH_2CH_2$—(O—$CH_2CH_2$—)$_4$O—$CH_2CH_2$—.

Alkoxy containing up to 18 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy. Preference is given to alkoxy containing from 1 to 12, especially from 1 to 8, for example from 1 to 6, carbon atoms.

$C_2$-$C_{18}$Alkoxy interrupted by oxygen or by sulfur is, for example, $CH_3$—O—$CH_2CH_2$O—, $CH_3$—S—$CH_2CH_2$O—, $CH_3$—O—$CH_2CH_2$—O—$CH_2CH_2$O—, $CH_3$—(O—$CH_2CH_2$—)$_2$O—$CH_2CH_2$O—, $CH_3$—(O—$CH_2CH_2$—)$_3$O—$CH_2CH_2$O— or $CH_3$—(O—$CH_2CH_2$—)$_4$O—$CH_2CH_2$O—.

$C_2$-$C_{12}$Alkyl interrupted by oxygen or by sulfur is, for example, $CH_3$—O—$CH_2$—, $CH_3CH_2$—O—$CH_2CH_2$—, $CH_3$—S—$CH_2$—, $CH_3CH_2$—S—$CH_2CH_2$—, $CH_3$—O—$CH_2CH_2$—O—$CH_2$—, $CH_3CH_2$—O—$CH_2CH_2$—O—$CH_2CH_2$—, $CH_3$—(O—$CH_2CH_2$—)$_2$O—$CH_2$—, $CH_3CH_2$—(O—$CH_2CH_2$—)$_2$O—$CH_2CH_2$—, $CH_3$—(O—$CH_2CH_2$—)$_3$O—$CH_2$—, $CH_3$—(O—$CH_2CH_2$—)$_4$O—$CH_2$— or $CH_3CH_2$—(O—$CH_2CH_2$—)$_4$O—$CH_2CH_2$—.

Alkenyl containing from 3 to 12 carbon atoms is a branched or unbranched radical, for example propenyl, 2-butenyl, 3-butenyl, isobutenyl, n-2,4-pentadienyl, 3-methyl-2-butenyl, n-2-octenyl, n-2-dodecenyl or isododecenyl.

$C_5$-$C_8$Cycloalkyl is, for example, cyclopentyl, cyclohexyl, cycloheptyl or cyclooctyl. Preference is given to cyclohexyl.

$C_7$-$C_{12}$Phenylalkyl is, for example, benzyl, α-methylbenzyl, α,α-dimethylbenzyl, 2-phenylethyl, 3-phenylpropyl, 4-phenylbutyl, 5-phenylpentyl or 6-phenylhexyl. Preference is given to benzyl and α,α-dimethylbenzyl.

Alkanoyl containing from 2 to 25 carbon atoms is a branched or unbranched radical, for example acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl.

An unsubstituted or $C_1$-$C_4$alkyl-substituted $C_5$-$C_{12}$cycloalkylidene ring containing preferably from 1 to 3, especially 1 or 2, branched or unbranched alkyl group radicals, is, for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Preference is given to cyclohexylidene.

Alkynyl containing from 3 to 6 carbon atoms is a branched or unbranched radical, for example propynyl

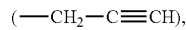

2-butynyl, 3-butynyl or n-2-hexynyl.

Acyl containing up to 8 carbon atoms is a branched or unbranched radical, for example formyl, acetyl, propionyl, butanoyl, pentanoyl, hexanoyloxy, heptanoyl or octanoyl.

Hydroxyalkoxy containing from 1 to 18 carbon atoms is a branched or unbranched radical containing preferably from 1 to 3, especially 1 or 2, hydroxy groups, for example hydroxyethoxy, 3-hydroxypropoxy, 2-hydroxypropoxy, 4-hydroxybutoxy, 3-hydroxybutoxy, 2-hydroxybutoxy, 5-hydroxypentyloxy, 4-hydroxypentyloxy, 3-hydroxypentyloxy, 2-hydroxypentyloxy, 6-hydroxyhexyloxy, 5-hydroxyhexyloxy, 4-hydroxyhexyloxy, 3-hydroxyhexyloxy, 2-hydroxyhexyloxy, 7-hydroxyheptyloxy, 6-hydroxyheptyloxy, 5-hydroxyheptyloxy, 4-hydroxyheptyloxy, 3-hydroxyheptyloxy, 2-hydroxyheptyloxy, 8-hydroxyoctyloxy, 7-hydroxyoctyloxy, 6-hydroxyoctyloxy, 5-hydroxyoctyloxy, 4-hydroxyoctyloxy, 3-hydroxyoctyloxy, 2-hydroxyoctyloxy, 9-hydroxynonyloxy, 10-hydroxydecyloxy, 11-hydroxyundecyloxy, 12-hydroxydodecyloxy, 13-hydroxytridecyloxy, 14-hydroxytetradecyloxy, 15-hydroxypentadecyloxy, 16-hydroxyhexadecyloxy, 17-hydroxyheptadecyloxy or 18-hydroxyoctadecyl.

Alkenyloxy containing from 2 to 18 carbon atoms is a branched or unbranched radical, for example vinyloxy, propenyloxy, 2-butenyloxy, 3-butenyloxy, isobutenyloxy, n-2,4-pentadienyloxy, 3-methyl-2-butenyloxy, n-2-octenyloxy, n-2-dodecenyloxy, isododecenyloxy, oleyloxy, n-2-octadecenyloxy or n-4-octadecenyloxy. Preference is given to alkenyloxy containing from 3 to 18, especially from 3 to 12, for example from 3 to 6, more especially 3 or 4, carbon atoms.

$C_5$-$C_{12}$Cycloalkoxy is, for example, cyclopentyloxy, cyclohexyloxy, cycloheptyloxy, cyclooctyloxy, cyclononyloxy, cyclodecyloxy, cycloundecyloxy or cyclododecyloxy. Preference is given to cyclohexyloxy.

Alkylidene containing from 2 to 8 carbon atoms is, for example, ethylidene, propylidene, butylidene, pentylidene, 4-methylpentylidene, heptylidene, octylidene, tridecylidene, 1-methylethylidene, 1-ethylpropylidene or 1-ethylpentylidene.

Halogen is, for example, chlorine, bromine or iodine. Preference is given to chlorine.

Of interest are polymers grafted with a compound of formula I wherein m or p is 1.

Preference is given to polymers grafted with a compound of formula I wherein,
when n is 0,
R is $C_1$-$C_{18}$alkyl, $C_2$-$C_{12}$hydroxyalkyl,

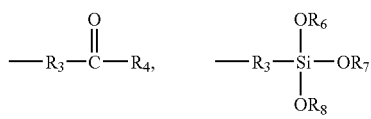

or a radical of formula II, III, IV, V, VI, VII, VIII or IX;
when n is 1,
R is $C_1$-$C_{12}$ alkylene,

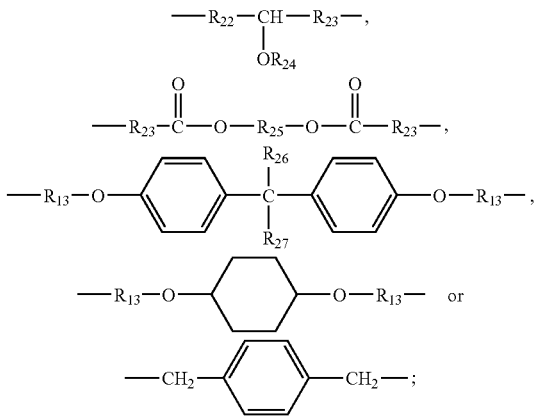

when n is 2,

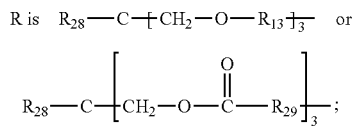

when n is 3,

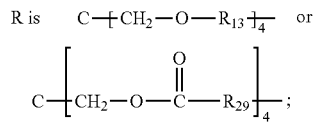

$R_1$ is $C_1$-$C_{18}$alkyl,

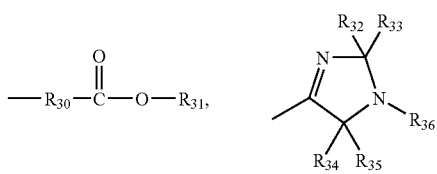

or $C_2$-$C_{12}$hydroxyalkyl,
$R_2$ is $C_1$-$C_{18}$alkyl,

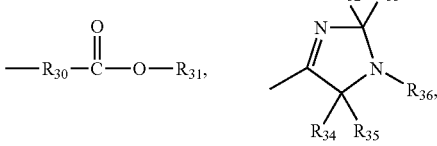

$C_2$-$C_{12}$hydroxyalkyl or a radical of formula III or IX,
$R_3$ is $C_1$-$C_{12}$alkylene, or $C_2$-$C_{12}$alkylene interrupted by oxygen,
$R_4$ is $C_1$-$C_{12}$alkoxy, or $C_3$-$C_{12}$alkoxy interrupted by oxygen, $R_5$ is $C_1$-$C_8$alkylene, or $C_2$-$C_8$alkylene interrupted by oxygen, $R_6$, $R_7$ and $R_8$ are each independently of the others hydrogen, $C_1$-$C_8$alkyl, $C_2$-$C_8$alkyl interrupted by oxygen; or $C_3$-$C_8$alkenyl, $R_9$ is hydrogen, $C_1$-$C_8$alkyl, cyclohexyl, $C_7$-$C_9$phenylalkyl or phenyl, $R_{10}$ is $C_1$-$C_8$alkyl, cyclohexyl, $C_7$-$C_9$phenylalkyl, phenyl,

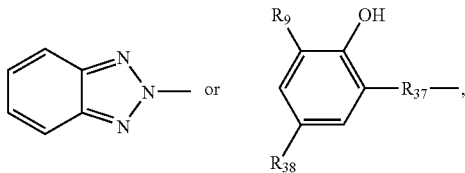

$R_{11}$ is a direct bond or $C_1$-$C_8$alkylene,
$R_{12}$ is a direct bond or $C_1$-$C_8$alkylene,
$R_{13}$ is $C_1$-$C_8$alkylene or

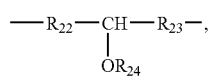

$R_{14}$ is hydrogen or $C_1$-$C_4$alkyl,
$R_{15}$ is $C_1$-$C_4$alkylene,
$R_{16}$ is hydrogen or $C_3$-$C_{12}$alkyl,
$R_{17}$ is $C_1$-$C_8$alkylene or

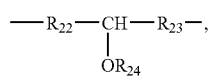

$R_{18}$ is hydrogen, $C_1$-$C_8$alkyl or a radical of formula II,
$R_{19}$ is $C_1$-$C_8$alkyl or $C_7$-$C_9$phenylalkyl,
$R_{20}$ is $C_1$-$C_8$alkyl or $C_7$-$C_9$phenylalkyl,
$R_{21}$ is

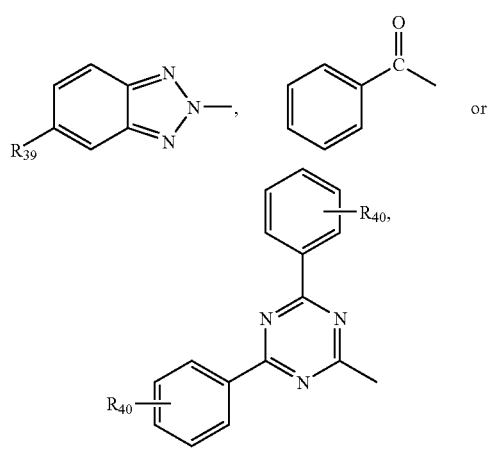

$R_{22}$ is a direct bond or $C_1$-$C_6$alkylene,
$R_{23}$ is $C_1$-$C_6$alkylene,
$R_{24}$ is hydrogen, $C_1$-$C_{18}$alkyl, $C_2$-$C_{18}$alkanoyl,

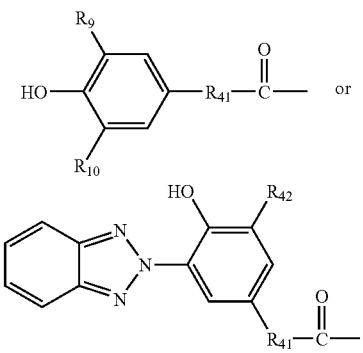

$R_{25}$ is $C_2$-$C_{13}$alkylene, or $C_2$-$C_{12}$alkylene interrupted by oxygen, $R_{26}$ and $R_{27}$ are each independently of the other hydrogen or $C_1$-$C_8$alkyl, or $R_{26}$ and $R_{27}$, together with the carbon atom to which they are bonded, form a $C_5$-$C_8$cycloalkylidene ring, $R_{28}$ is $C_1$-$C_4$alkyl,
$R_{29}$ is $C_1$-$C_8$alkylene,
$R_{30}$ is $C_1$-$C_4$alkylene,
$R_{31}$ is $C_2$-$C_{18}$alkyl,
$R_{32}$, $R_{33}$, $R_{34}$ and $R_{35}$ are each independently of the others $C_1$-$C_4$alkyl; or the radicals $R_{32}$ and $R_{33}$ or the radicals $R_{34}$ and $R_{35}$, together with the carbon atom to which they are bonded, form a $C_5$-$C_{12}$cycloalkylidene ring, $R_{36}$ is hydrogen, $C_1$-$C_{12}$alkyl, $C_3$-$C_6$alkenyl, benzyl, $C_1$-$C_8$acyl, $C_1$-$C_{12}$alkoxy, $C_1$-$C_{12}$hydroxyalkoxy, $C_2$-$C_{12}$alkenyloxy or $C_5$-$C_8$cycloalkoxy, $R_{37}$ is $C_1$-$C_4$alkylene, sulfur or $C_2$-$C_4$alkylidene,
$R_{38}$ is hydrogen, $C_1$-$C_6$alkyl, cyclohexyl or phenyl,
$R_{39}$ is hydrogen, chlorine, bromine, —SO—$C_1$-$C_{18}$alkyl or —$SO_2$—$C_1$-$C_{18}$alkyl,
$R_{40}$ is hydrogen, $C_1$-$C_6$alkyl or phenyl,
$R_{41}$ is a direct bond or $C_1$-$C_8$alkylene,
$R_{42}$ is hydrogen, $C_1$-$C_8$alkyl, cyclohexyl or $C_7$-$C_9$phenylalkyl,
m is 0, 1 or 2,
n is 0, 1, 2 or 3, and
p is 1 or 2.

Preference is given also to polymers grafted with a compound of formula I wherein,
when n is 0,
R is $C_1$-$C_{12}$alkyl, $C_2$-$C_8$hydroxyalkyl,

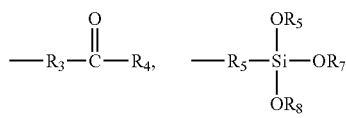

or a radical of formula II, III, IV, V, VI, VII, VIII or IX;
when n is 1,
R is $C_1$-$C_8$alkylene,

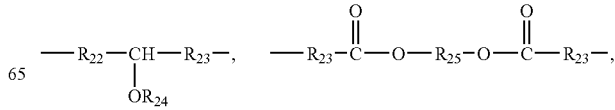

-continued

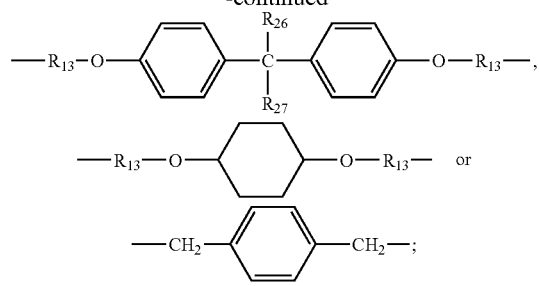

when n is 2,
R is

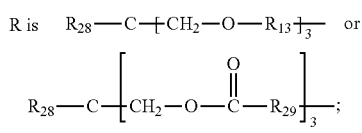

when n is 3,

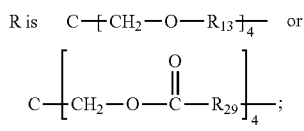

$R_1$ is $C_4$-$C_{18}$alkyl,

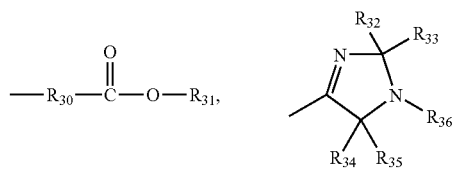

or $C_2$-$C_8$hydroxyalkyl,
$R_2$ is $C_4$-$C_{18}$alkyl,

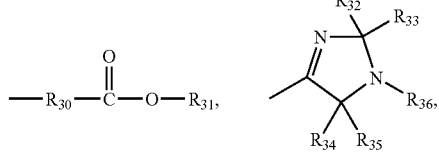

$C_2$-$C_8$hydroxyalkyl or a radical of formula III or IX,
$R_3$ is $C_1$-$C_8$alkylene,
$R_4$ is $C_1$-$C_8$alkoxy,
$R_5$ is $C_1$-$C_8$alkylene,
$R_6$, $R_7$ and $R_8$ are each independently of the others hydrogen, $C_1$-$C_8$alkyl or $C_3$-$C_8$alkenyl,
$R_9$ is $C_1$-$C_8$alkyl, cyclohexyl or $C_7$-$C_9$phenylalkyl,
$R_{10}$ is $C_1$-$C_8$alkyl, cyclohexyl, $C_7$-$C_9$phenylalkyl,

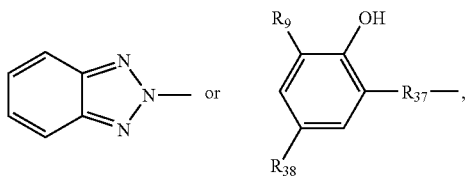

$R_{11}$ is $C_1$-$C_8$alkylene,
$R_{12}$ is $C_1$-$C_8$alkylene;
$R_{13}$ is $C_1$-$C_8$alkylene or

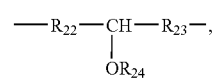

$R_{14}$ is $C_1$-$C_4$alkyl,
$R_{15}$ is $C_1$-$C_4$alkylene,
$R_{16}$ is $C_3$-$C_8$alkyl,
$R_{17}$ is $C_1$-$C_8$alkylene or

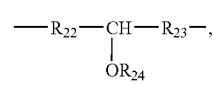

$R_{18}$ is hydrogen or $C_1$-$C_8$alkyl,
$R_{19}$ is $C_1$-$C_8$alkyl or $C_7$-$C_9$phenylalkyl,
$R_{20}$ is $C_1$-$C_8$alkyl or $C_7$-$C_9$phenylalkyl,
$R_{21}$ is

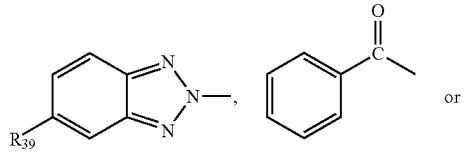

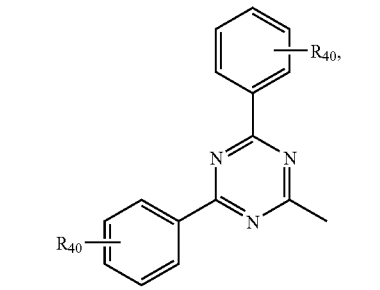

$R_{22}$ is $C_1$-$C_6$alkylene,
$R_{23}$ is $C_1$-$C_6$alkylene,
$R_{24}$ is hydrogen, $C_1$-$C_{12}$alkyl, $C_2$-$C_{12}$alkanoyl,

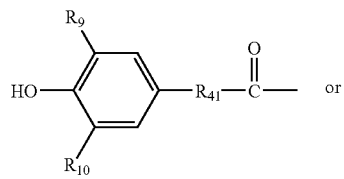

-continued

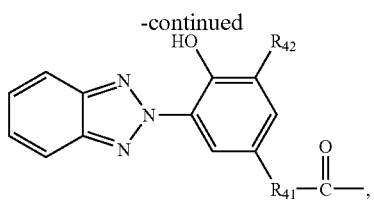

$R_{25}$ is $C_2$-$C_8$alkylene,
$R_{26}$ and $R_{27}$ are each independently of the other hydrogen or $C_1$-$C_4$alkyl, or $R_{26}$ and $R_{27}$, together with the carbon atom to which they are bonded, form a cyclohexylidene ring,
$R_{28}$ is $C_1$-$C_4$alkyl,
$R_{29}$ is $C_1$-$C_4$alkylene,
$R_{30}$ is $C_1$-$C_4$alkylene,
$R_{31}$ is $C_4$-$C_{18}$alkyl,
$R_{32}$, $R_{33}$, $R_{34}$ and $R_{35}$ are each independently of the others $C_1$-$C_4$alkyl; or the radicals $R_{32}$ and
$R_{33}$ or the radicals $R_{34}$ and $R_{35}$, together with the carbon atom to which they are bonded, form a cyclohexylidene ring,
$R_{36}$ is hydrogen, $C_1$-$C_8$alkyl, benzyl, $C_1$-$C_8$acyl, $C_1$-$C_8$alkoxy, $C_2$-$C_8$hydroxyalkoxy, $C_3$-$C_8$-alkenyloxy or cyclohexyloxy,
$R_{37}$ is $C_1$-$C_4$alkylene or $C_2$-$C_4$alkylidene,
$R_{38}$ is hydrogen, $C_1$-$C_4$alkyl or cyclohexyl,
$R_{39}$ is hydrogen, chlorine, —SO—$C_1$-$C_{12}$alkyl or —$SO_2$—$C_1$-$C_{12}$alkyl,
$R_{40}$ is hydrogen or $C_1$-$C_4$alkyl,
$R_{41}$ is $C_1$-$C_8$alkylene,
$R_{42}$ is $C_1$-$C_8$alkyl, cyclohexyl or $C_7$-$C_9$phenylalkyl,
m is 0, 1 or 2,
n is 0, 1, 2 or 3, and
p is 1 or 2.

The compounds of formula I are prepared, for example, by oxidation of the corresponding sulfides using peroxides. The corresponding sulfides are, in some cases, known from the literature or can be prepared in analogy to, for example, the examples given in U.S. Pat. No. 3,954,839.

Oxidation using peroxides is carried out preferably in the presence of a suitable protic or aprotic solvent, for example acetone.

The reaction is carried out at temperatures of, for example, from 0 to 60° C., especially from room temperature to 45° C.

A suitable and especially preferred oxidising agent is, for example, hydrogen peroxide.

The oxidation of sulfides using an oxidising agent such as, for example, hydrogen peroxide may also result in sulfoxides or sulfones which, when n=1, have been oxidised at only one sulfur, thereby giving rise to mixtures of compounds that either are oxidised at the sulfur in question or are not. Any conceivable permutation is possible. Those mixtures are likewise suitable as grafting agents for polymers for the purpose of protecting the latter against oxidative, thermal, dynamic, light-induced and/or ozone-induced degradation.

Suitable polymers that may be grafted with a compound of formula I are, for example:
1. Polymers of mono- and di-olefins, for example polypropylene, polyisobutylene, polybutene-1, poly-4-methylpentene-1, polyvinylcyclohexane, polyisoprene or polybutadiene and also polymerisates of cycloolefins, for example of cyclopentene or norbornene; and also polyethylene (which may optionally be cross-linked), for example high density polyethylene (HDPE), high density polyethylene of high molecular weight (HDPE-HMW), high density polyethylene of ultra-high molecular weight (HDPE-UHMW), medium density polyethylene (MDPE), low density polyethylene (LDPE), and linear low density polyethylene (LLDPE), (VLDPE) and (ULDPE).

Polyolefins, that is to say polymers of monoolefins, as mentioned by way of example in the preceding paragraph, especially polyethylene and polypropylene, can be prepared by various processes, especially by the following methods:
a) by free radical polymerisation (usually at high pressure and high temperature);
b) by means of a catalyst, the catalyst usually containing one or more metals of group IVb, Vb, VIb or VIII. Such metals generally have one or more ligands, such as oxides, halides, alcoholates, esters, ethers, amines, alkyls, alkenyls and/or aryls, which may be either π- or σ-coordinated. Such metal complexes may be free or fixed to carriers, for example to activated magnesium chloride, titanium(III) chloride, aluminium oxide or silicon oxide. Such catalysts may be soluble or insoluble in the polymerisation medium. The catalysts can be active as such in the polymerisation or further activators may be used, for example metal alkyls, metal hydrides, metal alkyl halides, metal alkyl oxides or metal alkyl oxanes, the metals being elements of group(s) Ia, IIa and/or IIIa. The activators may be modified, for example, with further ester, ether, amine or silyl ether groups. Such catalyst systems are usually known as Phillips, Standard Oil Indiana, Ziegler (-Natta), TNZ (DuPont), metallocene or Single Site Catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and di-olefins with one another or with other vinyl monomers, for example ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers, for example ethylene/norbornene (COC), ethylene/1-olefin copolymers wherein the 1-olefin is prepared in situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers, ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another and with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide copolymers and mixtures thereof with other polymers, for example polyamides.

4. Hydrocarbon resins (for example $C_{5-9}$) including hydrogenated modifications thereof (for example tackifier resins) and mixtures of polyalkylenes and starch.

Homopolymers and copolymers according to 1.) to 4.) can have a syndiotactic, isotactic, semi-isotactic or atactic stereo structure; preference is given to atactic polymers. Stereoblock polymers are also included.

5. Polystyrene, poly(p-methylstyrene), poly(α-methylstyrene).

6. Aromatic homopolymers and copolymers derived from vinyl-aromatic monomers, for example styrene, α-methylstyrene, all isomers of vinyltoluene, for example p-vinyltoluene, all isomers of ethylstyrene, propylstyrene, vinylbiphenyl, vinylnaphthalene, vinylanthracene and mixtures thereof; homopolymers and copolymers can have a syndiotactic, isotactic, semi-isotactic or atactic stereo structure; preference is given to atactic polymers. Stereoblock polymers are also included.

6a. Copolymers including the already mentioned vinyl-aromatic monomers and comonomers selected from ethylene, propylene, dienes, nitriles, acids, maleic anhydrides, maleic acid amides, vinyl acetate, vinyl chloride and acrylic acid derivatives and mixtures thereof, for example styrene/butadiene, styrene/acrylonitrile, styrene/ethylene (interpolymers), styrene/alkyl methacrylate, styrene/butadiene/alkyl acrylate and methacrylate, styrene/maleic anhydride, styrene/acrylonitrile/methyl acrylate; high-impact-strength mixtures consisting of styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene.

6b. Hydrogenated aromatic polymers prepared by hydrogenation of the polymers mentioned under 6.), especially polycyclohexylethylene (PCHE), often also referred to as polyvinylcyclohexane (PVCH), which is prepared by hydrogenation of atactic polystyrene.

6c. Hydrogenated aromatic polymers prepared by hydrogenation of the polymers mentioned under 6a.).

Homopolymers and copolymers can have a syndiotactic, isotactic, semi-isotactic or atactic stereo structure; preference is given to atactic polymers. Stereoblock polymers are also included.

7. Graft copolymers of vinyl-aromatic monomers, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 6), such as those known, for example, as so-called ABS, MBS, ASA or AES polymers.

8. Halogen-containing polymers, for example polychloroprene, chlorinated rubber, chlorinated and brominated copolymer of isobutylene/isoprene (halobutyl rubber), chlorinated or chlorosulfonated polyethylene, copolymers of ethylene and chlorinated ethylene, epichlorohydrin homo- and co-polymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers derived from α,β-unsaturated acids and derivatives thereof, such as polyacrylates and polymethacrylates, and polymethyl methacrylates, polyacrylamides and polyacrylonitriles impact-resistant-modified with butyl acrylate.

10. Copolymers of the monomers mentioned under 9) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines or their acyl derivatives or acetals, such as polyvinyl alcohol, polyvinyl acetate, stearate, benzoate or maleate, polyvinylbutyral, polyallyl phthalate, polyallylmelamine; and the copolymers thereof with olefins mentioned in Point 1.

12. Homo- and co-polymers of cyclic ethers, such as polyalkylene glycols, polyethylene oxide, polypropylene oxide or copolymers thereof with bisglycidyl ethers.

13. Polyacetals, such as polyoxymethylene, and also those polyoxymethylenes which contain comonomers, for example ethylene oxide; polyacetals that are modified with thermoplastic polyurethanes, acrylates or MBS.

14. Polyphenylene oxides and sulfides and mixtures thereof with styrene polymers or polyamides.

15. Polyurethanes derived from polyethers, polyesters and polybutadienes having terminal hydroxyl groups on the one hand and aliphatic or aromatic polyisocyanates on the other hand, and their initial products.

16. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides derived from m-xylene, diamine and adipic acid; polyamides prepared from hexamethylenediamine and iso- and/or tere-phthalic acid and optionally an elastomer as modifier, for example poly-2,4,4-trimethylhexamethylene terephthalamide or poly-m-phenylene isophthalamide; block copolymers of the above-mentioned polyamides with polyolefins, olefin copolymers, ionomers or chemically bonded or grafted elastomers, or with polyethers, for example with polyethylene glycol, polypropylene glycol or polytetramethylene glycol; also polyamides or copolyamides modified with EPDM or ABS; and polyamides condensed during processing ("RIM polyamide systems").

17. Polyureas, polyimides, polyamide imides, polyether imides, polyester imides, polyhydantoins and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyalkylene naphthalate (PAN) and polyhydroxybenzoates, and also block polyether esters derived from polyethers with hydroxyl terminal groups; and also polyesters modified with polycarbonates or MBS.

19. Polycarbonates and polyester carbonates.

20. Polyketones.

21. Polysulfones, polyether sulfones and polyether ketones.

22. Cross-linked polymers derived from aldehydes on the one hand and phenols, urea or melamine on the other hand, such as phenol-formaldehyde, urea-formaldehyde and melamine-formaldehyde resins.

23. Drying and non-drying alkyd resins.

24. Unsaturated polyester resins derived from copolyesters of saturated and unsaturated dicarboxylic acids with polyhydric alcohols, and also vinyl compounds as cross-linking agents, and also the halogen-containing modifications thereof that are not readily combustible.

25. Cross-linkable acrylic resins derived from substituted acrylic acid esters, e.g. from epoxy acrylates, urethane acrylates or polyester acrylates.

26. Alkyd resins, polyester resins and acrylate resins that are cross-linked with melamine resins, urea resins, isocyanates, isocyanurates, polyisocyanates or epoxy resins.

27. Cross-linked epoxy resins derived from aliphatic, cycloaliphatic, heterocyclic or aromatic glycidyl compounds, e.g. products of diglycidyl ethers of bisphenol A, diglycidyl ethers of bisphenol F, that are cross-linked using customary hardeners, e.g. anhydrides or amines with or without accelerators.

28. Natural polymers, such as cellulose, natural rubber, gelatin, and polymer-homologously chemically modified derivatives thereof, such as cellulose acetates, propionates and butyrates, and the cellulose ethers, such as methyl cellulose; and also colophony resins and derivatives.

29. Mixtures (polyblends) of the afore-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

30. Natural and synthetic organic substances that are pure monomeric compounds or mixtures thereof, for example mineral oils, animal or vegetable fats, oils and waxes, or oils, waxes and fats based on synthetic esters (for example phthalates, adipates, phosphates or trimellitates), and admixtures of synthetic esters with mineral oils in any weight ratios, as used, for example, as spin-coating preparations, and aqueous emulsions thereof.

31. Aqueous emulsions of natural or synthetic rubbers, for example natural rubber latex or latexes of carboxylated styrene/butadiene copolymers.

Of special interest are natural, semi-synthetic or synthetic polymers, for example polyolefins, styrene copolymers and elastomers.

Especially preferred polyolefins are polyethylene and polypropylene.

Elastomers are to be understood as macromolecular materials that at room temperature after considerable deformation under low stress are capable of returning rapidly to virtually their original shape. See also Hans-Georg Elias, "An Introduction to Polymer Science", Chapter 12. "Elastomers", pages 388-393, 1997, VCH Verlagsgesellschaft mbH, Weinheim, Germany; or "Ullmann's Encyclopedia of Industrial Chemistry, Fifth, Completely Revised Edition, Volume A 23", pages 221-440 (1993).

The compounds of formula I are added to the polymer to be grafted in an amount of, advantageously, from 0.05 to 10%, for example from 0.1 to 5%, preferably from 0.5 to 3.0%, based on the weight of the polymer to be grafted.

The ungrafted or grafted polymers may additionally comprise further additives, for example the following:

1. Antioxidants
1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear nonylphenols or nonylphenols branched in the side-chain, e.g. 2,6-dinonyl-4-methylphenol, 2,4-dimethyl-6-(1'-methylundec-1'-yl)-phenol, 2,4-dimethyl-6-(1'-methylheptadec-1'-yl)-phenol, 2,4-dimethyl-6-(1'-methyltridec-1'-yl)-phenol and mixtures thereof.

1.2. Alkylthiomethylphenols, for example 2,4-dioctylthiomethyl-6-tert-butylphenol, 2,4-dioctyl-thiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidene bisphenols, for example 2,2'-methylenebis (6-tert-butyl-4-methylphenol), 2,2'-methylenebis (6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tertbutylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra (5-tert-butyl-4-hydroxy-2-methylphenyl)pentane.

1.7. O-, N- and S-benzyl compounds, for example 3,5,3', 5'-tetra-tert-butyl-4,4'-dihydroxydibenzyl ether, octadecyl-4-hydroxy-3,5-dimethylbenzyl mercaptoacetate, tridecyl-4-hydroxy3,5-di-tert-butylbenzyl mercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide, isooctyl-3,5-di-tert-butyl-4-hydroxybenzyl mercaptoacetate.

1.8. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl)malonate, didodecylmercaptoethyl 2,2-bis(3,5-di-tert-butyl-4-hydroxybenzyl)malonate, di-[4-(1,1,3,3-tetramethylbutyl) phenyl] 2,2-bis(3,5-di-tert-butyl-4-hydroxybenzyl) malonate.

1.9. Hydroxybenzyl aromatic compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3, 5,6-tetramethylbenzene, 2,4,6-tris(3,5-di-tert-butyl-4-hydroxybenzyl)phenol.

1.10. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxy-benzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxy-benzyl) isocyanurate.

1.11. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, calcium salt of 3,5-di-tert-butyl-4-hydroxybenzyl-phosphonic acid monoethyl ester.

1.12. Acylaminophenols, for example 4-hydroxylauric acid anilide, 4-hydroxystearic acid anilide, N-(3,5-di-tert-butyl-4-hydroxyphenyl)carbamic acid octyl ester.

1.13. Esters of β-(3,5-di-tert-butyl-4-hydroxyphenyl)propionic acid with mono- or poly-hydric alcohols, for example with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, for example with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl)propionic acid with mono- or poly-hydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenylacetic acid with mono- or poly-hydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid, for example N,N'-bis(3,5-di-tert-butyl4-hydroxyphenylpropionyl)hexamethylenediamide, N,N'-bis(3,5-di-tert-butyl4-hydroxyphenylpropionyl) trimethylenediamide, N,N'-bis(3,5-di-tert-butyl-4-hydroxyphenyl-propionyl)hydrazide), N,N'-bis[2-(3-[3,5-di-tert-butyl-4-hydroxyphenyl]-propionyloxy)ethyl]-oxamide (Naugard®XL-1 from Uniroyal).

1.18. Ascorbic acid (Vitamin C).

1.19. Amine-type antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-allyldiphenylamine,4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di(4-methoxyphenyl)amine, 2,6-di-tert-butyl-4-dimethylaminomethylphenol, 2,4'-diaminodiphenylmethane, 4,4'-diaminodiphenylmethane, N,N,N', N'-tetramethyl-4,4'-diaminodiphenylmethane, 1,2-di[(2-methylphenyl)amino]ethane, 1,2-di(phenylamino)propane, (o-tolyl)-biguanide, di[4-(1', 3'-dimethylbutyl)phenyl]amine, tert-octylated N-phenyl-1-naphthylamine, mixture of mono- and di-alkylated tert-butyl-/tert-octyl-diphenylamines, mixture of mono- and di-alkylated nonyldiphenylamines, mixture of mono- and di-alkylated dodecyldiphenylamines, mixture of mono- and di-alkylated isopropyl-/isohexyl-diphenylamines, mixtures of mono- and di-alkylated tertbutyldiphenylamines, 2,3-dihydro-3,3-dimethyl4H-1,4-benzothiazine, phenothiazine, mixture of mono- and di-alkylated tert-butyl-/tert-octyl-phenothiazines, mixture of mono- and di-alkylated tert-octylphenothiazines, N-allylphenothiazine or N,N,N',N'-tetraphenyl-1,4-diaminobut-2-ene.

2. UV Absorbers and Light Stabilisers 2.1. 2-(2'-Hydroxyphenyl)-benzotriazoles, for example 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)-phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3', 5'-di-tert-amyl-2'-hydroxyphenyl)-benzotriazole, 2-(3',5'-bis (α,α-dimethylbenzyl)-2'-hydroxyphenyl)-benzotriazole, 2-(3'-tert-butyl-2'-hydroxy-5'-(2-octyloxycarbonylethyl) phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)-benzotriazole, 2-(3'-tert-butyl-2'-hydroxy-5'-(2-isooctyloxycarbonylethyl)-phenylbenzotriazole, 2,2'-methylenebis[4-(1,1,3,3-tetramethylbutyl)-6-benzotriazol- 2-yl-phenol]; transesterification product of 2-[3'-tert-butyl-5'-(2-methoxycarbonylethyl)-2'-hydroxyphenyl]-benzotriazole with polyethylene glycol 300; [R—CH$_2$CH$_2$—COO—CH$_2$CH$_2$—]$_2$ wherein R=3'-tert-butyl-4'-hydroxy-5'-2H-benzotriazol-2-yl-phenyl; 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.

2.3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.

2.4. Acrylates, for example α-cyano-β,β-diphenylacrylic acid ethyl ester or isooctyl ester, α-methoxycarbonylcinnamic acid methyl ester, α-cyano-β-methyl-p-methoxycinnamic acid methyl ester or butyl ester, α-methoxycarbonyl-p-methoxycinnamic acid methyl ester, N-(β-methoxycarbonyl-β-cyanovinyl)-2-methyl-indoline.

2.5. Nickel compounds, for example nickel complexes of 2,2'-thio-bis[4-(1,1,3,3-tetramethylbutyl)phenol], such as the 1:1 or 1:2 complex, optionally with additional ligands, such as n-butylamine, triethanolamine or N-cyclohexyldiethanolamine, nickel dibutyl dithiocarbamate, nickel salts of 4-hydroxy-3,5-di-tert-butylbenzylphosphonic acid monoalkyl esters, such as of the methyl or ethyl ester, nickel complexes of ketoximes, such as of 2-hydroxy4-methylphenylundecyl ketoxime, nickel complexes of 1-phenyl-4-lauroyl-5-hydroxypyrazole, optionally with additional ligands.

2.6. Sterically hindered amines, for example bis(2,2,6,6-tetramethylpiperid-4-yl) sebacate, bis(2,2,6,6-tetramethylpiperid4-yl) succinate, bis(1,2,2,6,6-pentamethylpiperid-4-yl) sebacate, bis(1-octyloxy-2,2,6,6-tetramethylpiperid-4-yl) sebacate, n-butyl-3,5-di-tert-butyl-4-hydroxybenzylmalonic acid bis(1,2,2,6,6-pentamethylpiperidyl) ester, condensation product of 1-hydroxyethyl-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl)-1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensation products of N,N'-bis(2,2,6,6-tetramethyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, mixture of 4-hexadecyloxy- and 4-stearyloxy-2,2,6,6-tetramethylpiperidine, condensation product of N,N'-bis(2,2,6,6-tetramethyl-4-piperidyl) hexamethylenediamine and 4-cyclohexylamino-2,6-dichloro-1,3,5-triazine, condensation product of 1,2-bis(3-aminopropylamino)ethane and 2,4,6-trichloro-1,3,5-triazine and 4-butylamino-2,2,6,6-tetramethylpiperidine (CAS Reg. No. [136504-96-6]); condensation product of 1,6-diaminohexane and 2,4,6-trichloro-1,3,5-triazine and also N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4.5]decane, reaction product of 7,7,9,9-tetramethyl-2-cycloundecyl-1-oxa-3,8-diaza-4-oxospiro[4.5]decane and epichlorohydrin, 1,1-bis(1,2,2,6,6-pentamethyl4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic anhydride α-olefin copolymer and 2,2,6,6-tetramethyl-4-aminopiperidine or 1,2,2,6,6-pentamethyl-4-aminopiperidine.

2.7. Oxalic acid diamides, for example 4,4'-dioctyloxy oxanilide, 2,2'-diethoxy oxanilide, 2,2'-dioctyloxy-5,5'-di-tert-butyl oxanilide, 2,2'-didodecyloxy-5,5'-di-tert-butyl oxanilide, 2-ethoxy-2'-ethyl oxanilide, N,N'-bis(3-dimethylaminopropyl) oxalamide, 2-ethoxy-5-tert-butyl-2'-ethyl oxanilide and a mixture thereof with 2-ethoxy-2'-ethyl-5,4'-di-tert-butyl oxanilide, mixtures of o- and p-methoxy- and also of o- and p-ethoxy-di-substituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy) phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxy-propyloxy]phenyl}-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis (salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide, oxanilide, isophthalic acid dihydrazide, sebacic acid bis-phenylhydrazide, N,N'-diacetyladipic acid dihydrazide, N,N'-bis-salicyloyloxalic acid dihydrazide, N,N'-bis-salicyloylthiopropionic acid dihydrazide.

4. Phosphites and phosphonites, e.g. triphenyl phosphite, diphenylalkyl phosphites, phenyldialkyl phosphites, tris(nonylphenyl)phosphite, trilauryl phosphite, trioctadecyl phosphite, distearyl-pentaerythritol diphosphite, tris(2,4-di-tert-butylphenyl)phosphite, diisodecylpentaerythritol diphosphite, bis(2,4-di-tert-butylphenyl)pentaerythritol diphosphite, bis(2,4-di-cumylphenyl)-pentaerythritol diphosphite, bis(2,6-di-tert-butyl-4-methylphenyl)pentaerythritol diphosphite, bis-isodecyloxy-pentaerythritol diphosphite, bis(2,4-di-tert-butyl-6-methylphenyl)pentaerythritol diphosphite, bis(2,4,6-tri-tert-butylphenyl)pentaerythritol diphosphite, tristearyl sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, bis(2,4-di-tert-butyl-6-methylphenyl) methylphosphite, bis(2,4-di-tert-butyl-6-methylphenyl) ethylphosphite, 6-fluoro-2,4,8,10-tetra-tert-butyl-12-methyl-dibenzo[d,g]-1,3,2-dioxaphosphocine, 2,2',2''-nitrilo[triethyl-tris(3,3',5,5'-tetra-tert-butyl-1,1'-biphenyl-2,2'-diyl)-phosphite], 2-ethylhexyl-(3,3',5,5'-tetra-tert-butyl-1,1'-biphenyl-2,2'-diyl) phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine from hydrogenated tallow fatty amines.

6. Nitrones, for example N-benzyl-alpha-phenylnitrone, N-ethyl-alpha-methylnitrone, N-octylalpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-octadecyl-alpha-pentadecylnitrone, N-heptadecyl-alpha-hepta-decylnitrone, N-octadecyl-alpha-hexadecylnitrone, nitrones derived from N,N-dialkylhydroxylamines prepared from hydrogenated tallow fatty amines.

7. Thiosynergistic compounds, for example thiodipropionic acid dilauryl ester or thiodipropionic acid distearyl ester.

8. Peroxide-destroying compounds, for example esters of β-thio-dipropionic acid, for example the lauryl, stearyl, myristyl or tridecyl ester, mercaptobenzimidazole, the zinc salt of 2-mercaptobenzimidazole, zinc dibutyldithiocarbamate, dioctadecyldisulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, for example calcium stearate, zinc stearate, magnesium behenate, magnesium stearate, sodium ricinoleate, potassium palmitate, antimony pyrocatecholate or zinc pyrocatecholate.

11. Nucleating agents, for example inorganic substances, e.g. talc, metal oxides, such as titanium dioxide or magnesium oxide, phosphates, carbonates or sulfates of preferably alkaline earth metals; organic compounds, such as mono- or poly-carboxylic acids and their salts, e.g. 4-tert-butylbenzoic acid, adipic acid, diphenylacetic acid, sodium succinate or sodium benzoate; polymeric compounds, for example ionic copolymerisates ("ionomers"). Special preference is given to 1,3:2,4-bis(3',4'-dimethylbenzylidene)sorbitol, 1,3:2,4-di(paramethyldibenzylidene)sorbitol and 1,3:2,4-di(benzylidene)sorbitol.

12. Fillers and reinforcing agents, for example calcium carbonate, silicates, glass fibres, glass beads, talc, kaolin, mica, barium sulfate, metal oxides and hydroxides, carbon black, graphite, wood powders, and powders and fibres of other natural products, synthetic fibres.

13. Other additives, for example plasticisers, lubricants, emulsifiers, pigments, rheology additives, catalysts, flow improvers, optical brighteners, flame retardants, antistatics, blowing agents.

14. Benzofuranones and indolinones, for example as described in U.S. Pat. Nos. 4,325,863; 4,338,244; 5,175,312, 5,216,052; 5,252,643; DE-A-4 316 611; DE-A-4 316 622; DE-A-4 316 876; EP-A-0 589 839 or EP-A-0 591 102, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxy-phenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The present invention accordingly relates also to compositions comprising a) a polymer which is subject to oxidative, thermal, dynamic, light-induced and/or ozone-induced degradation and which has been grafted with a compound of formula I, and b), as additive, at least one compound selected from the group pigments, dyes, fillers, flow improvers, dispersing agents, plasticisers, vulcanisation activators, vulcanisation accelerators, vulcanisation agents, charge control agents, adhesion promoters, antioxidants and light stabilisers.

Preferred additives in the compositions according to the invention are, for example, antioxidants, e.g. phenolic antioxidants (points 1.1 to 1.17 of the list) or amine-type antioxidants (point 1.19 of the list), organic phosphites or phosphonites (point 4 of the list) and/or thiosynergistic compounds (point 7 of the list).

The additional additives are added, for example, in concentrations of from 0.01 to 10%, based on the total weight of the polymer.

The grafting of the polymers and also, where applicable, the incorporation of further additives into the polymers are carried out according to known methods, for example during mixing in internal (Banbury) mixers, on mixing roll mills or in mixing extruders, before or during shaping or vulcanisation (in the case of elastomers) or also by application of the dissolved or dispersed compounds of formula I to the polymers, where appropriate with subsequent evaporation of the solvent. The compounds of formula I and, where applicable, further additives can also be added, to the polymer being grafted, in the form of a masterbatch containing them in a concentration of, for example, from 2.5 to 25% by weight.

The compounds of formula I and, where applicable, further additives can also be added before or during the polymerisation of polymers. In the case of crude rubber, the compounds of formula I, together with further components, for example carbon black as filler and/or extender oils, can be added during cross-linking.

The compounds of formula I are chemically bonded (grafted) to polymer chains under processing conditions (mixing, vulcanisation etc.). The compounds of formula I are stable to extraction, that is to say they still possess good protective action after the substrate has been exposed to intensive extraction. The loss of compounds of formula I caused by migration or extraction from the polymers is extremely small.

The elastomers grafted with the compounds of formula I furthermore exhibit markedly improved, desirable gloss formation, which means that the surface gloss of the elastomer grafted in accordance with the invention is significantly greater, after exposure to the action of ozone, than that of a non-stabilised elastomer or of an elastomer stabilised in accordance with the prior art.

The compounds of formula I and, where applicable, further additives can be incorporated into the polymer being grafted in pure form or encapsulated in waxes, oils or polymers.

The compounds of formula I and, where applicable, further additives can also be sprayed onto the polymer being grafted. They are capable of diluting other additives (for example the customary additives mentioned hereinbefore) or melts thereof, so that they can also be sprayed together with those additives onto the polymer being grafted.

The polymers grafted in that manner can be used in a very wide variety of forms, for example as small bands, moulding materials, profiles, conveyor belts or tyres.

The present invention relates also to novel compounds of formula I

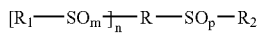

(I)

wherein, when n is 0,
R is $C_1$-$C_{25}$alkyl, $C_2$-$C_{18}$hydroxyalkyl,

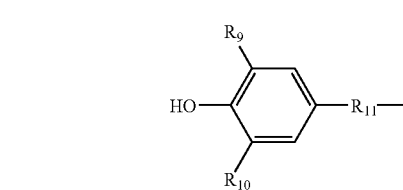

or a radical of formula II, III, IV, V, VI, VII or IX

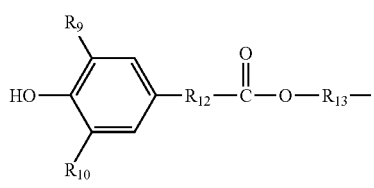

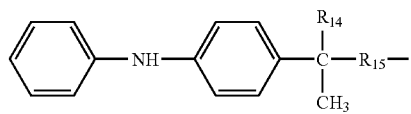

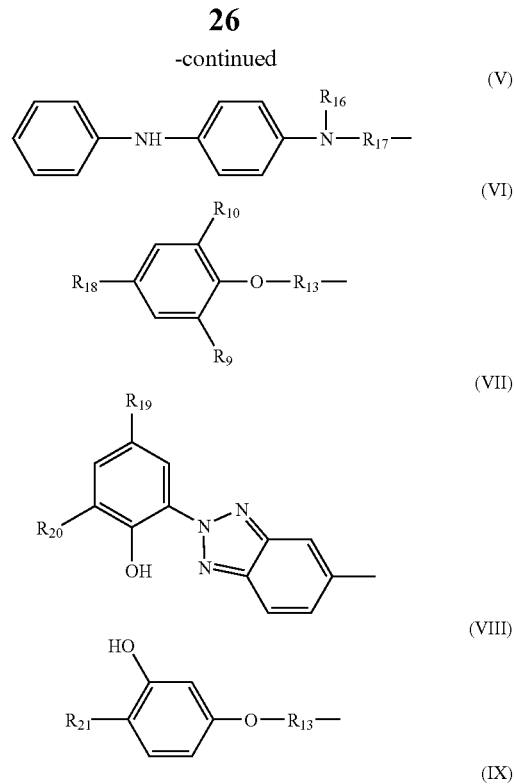

when n is 1,
R is $C_1$-$C_{18}$alkylene,

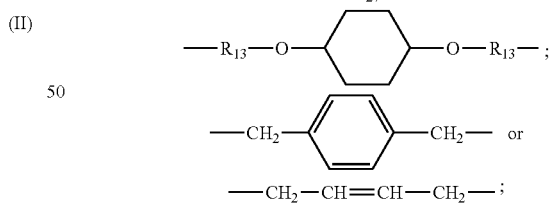

when n is 2,
R is

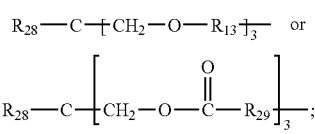

when n is 3,
R is

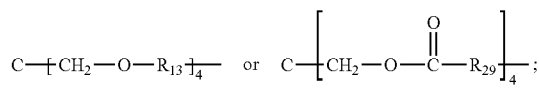

$R_1$ is $C_1$-$C_{25}$alkyl

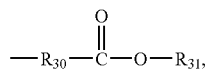 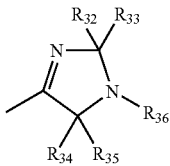

or $C_2$-$C_{18}$hydroxyalkyl,
$R_2$ is $C_1$-$C_{25}$alkyl,

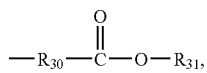 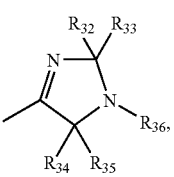

$C_2$-$C_{18}$hydroxyalkyl or a radical of formula III or IX,
$R_3$ is $C_1$-$C_{18}$alkylene, or $C_2$-$C_{18}$alkylene interrupted by oxygen or by sulfur,
$R_4$ is hydroxy, $C_1$-$C_{18}$alkoxy, or $C_3$-$C_{18}$alkoxy interrupted by oxygen or by sulfur,
$R_5$ is $C_1$-$C_{12}$alkylene, or $C_2$-$C_{12}$alkylene interrupted by oxygen,
$R_6$, $R_7$ and $R_8$ are each independently of the others hydrogen, $C_1$-$C_{12}$alkyl, $C_2$-$C_{12}$alkyl interrupted by oxygen or by sulfur; or $C_3$-$C_{12}$alkenyl,
$R_9$ is hydrogen, $C_1$-$C_8$alkyl, $C_5$-$C_8$cycloalkyl, $C_7$-$C_9$phenylalkyl or phenyl,
$R_{10}$ is $C_1$-$C_8$alkyl, $C_5$-$C_8$cycloalkyl, $C_7$-$C_9$phenylalkyl, phenyl,

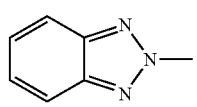 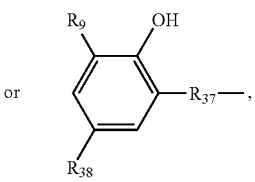

$R_{11}$ is a direct bond or unsubstituted or $C_1$-$C_4$alkyl-substituted $C_1$-$C_8$alkylene,
$R_{12}$ is a direct bond or unsubstituted or $C_1$-$C_4$alkyl-substituted $C_1$-$C_8$alkylene,
$R_{13}$ is $C_1$-$C_8$alkylene or

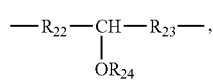

$R_{14}$ is hydrogen or $C_1$-$C_4$alkyl,
$R_{15}$ is $C_1$-$C_4$alkylene,
$R_{16}$ is hydrogen, cyclohexyl or $C_3$-$C_{12}$alkyl,
$R_{17}$ is $C_1$-$C_8$alkylene or

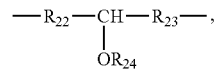

$R_{18}$ is hydrogen, $C_1$-$C_{12}$alkyl or a radical of formula II,
$R_{19}$ is $C_1$-$C_{12}$alkyl or $C_7$-$C_9$phenylalkyl,
$R_{20}$ is $C_1$-$C_{12}$alkyl or $C_7$-$C_9$phenylalkyl,
$R_{21}$ is

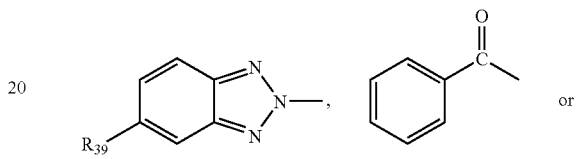

$R_{22}$ is a direct bond or $C_1$-$C_8$alkylene,
$R_{23}$ is $C_1$-$C_8$alkylene,
$R_{24}$ is hydrogen, $C_1$-$C_{25}$alkyl, $C_2$-$C_{25}$alkanoyl,

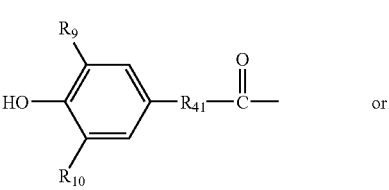

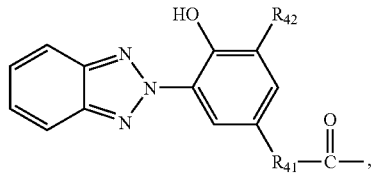

$R_{25}$ is $C_2$-$C_{18}$alkylene or $C_2$-$C_{18}$alkylene interrupted by oxygen or by sulfur,
$R_{26}$ and $R_{27}$ are each independently of the other hydrogen, $CF_3$, $C_1$-$C_{12}$alkyl or phenyl, or $R_{26}$ and $R_{27}$, together with the carbon atom to which they are bonded, form a $C_5$-$C_8$cycloalkylidene ring that is unsubstituted or substituted by from 1 to 3 $C_1$-$C_4$alkyl groups,
$R_{28}$ is $C_1$-$C_8$alkyl,
$R_{29}$ is $C_1$-$C_{12}$alkylene,
$R_{30}$ is $C_1$-$C_8$alkylene,
$R_{31}$ is $C_1$-$C_{25}$alkyl,
$R_{32}$, $R_{33}$, $R_{34}$ and $R_{35}$ are each independently of the others $C_1$-$C_8$alkyl; or the radicals $R_{32}$ and $R_{33}$ or the radicals $R_{34}$ and $R_{35}$, together with the carbon atom to which they are bonded, form a $C_5$-$C_{12}$cycloalkylidene ring, $R_{36}$ is hydrogen, $C_1$-$C_{18}$alkyl, $C_3$-$C_6$alkenyl, $C_3$-$C_6$alkynyl, $C_7$-$C_{12}$phenylalkyl, $C_1$-$C_8$acyl, $C_1$-$C_{18}$alkoxy, $C_1$-$C_{18}$hydroxyalkoxy, $C_2$-$C_{18}$alkenyloxy or $C_5$-$C_{12}$cycloalkoxy, $R_{37}$ is $C_1$-$C_4$alkylene, sulfur or $C_2$-$C_8$alkylidene, $R_{38}$ is hydrogen, $C_1$-$C_8$alkyl, $C_5$-$C_8$cycloalkyl or phenyl, $R_{39}$ is hydrogen, halogen, —SO—$C_1$-$C_{25}$alkyl or —$SO_2$—$C_1$-$C_{25}$alkyl, $R_{40}$ is hydrogen, $C_1$-$C_8$alkyl or phenyl, $R_{41}$ is a direct bond, or unsubstituted or $C_1$-$C_4$alkyl-substituted $C_1$-$C_8$alkylene, $R_{42}$ is hydrogen, $C_1$-$C_8$alkyl, $C_5$-$C_8$cycloalkyl or $C_7$-$C_9$phenylalkyl, m is 0, 1 or 2, n is 0, 1, 2 or 3, and p is 1 or 2;

with the proviso that, when n is 0, R is a radical of formula V, $R_{17}$ is

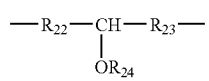

and $R_{22}$ and $R_{23}$ are methylene, then $R_{24}$ is other than hydrogen.

Preferred groups of novel compounds of formula I correspond to the preferences expressed hereinbefore for polymer grafting.

Of special interest are compounds of formula I wherein, when n is 0,

R is a radical of formula II or III

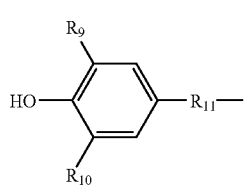

(II)

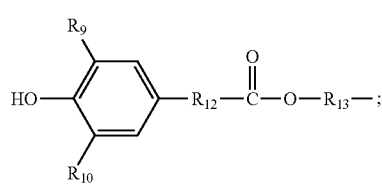

(III)

and, when n is 1,

R is

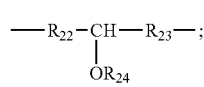

$R_1$ is $C_8$-$C_{12}$alkyl or

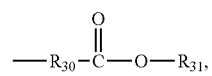

$R_2$ is $C_8$-$C_{12}$alkyl,

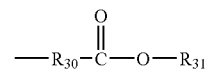

or a radical of formula III, $R_9$ is tert-butyl, $R_{10}$ is $C_1$-$C_4$alkyl, $R_{11}$ is methylene or ethylene, $R_{12}$ is ethylene, $R_{13}$ is ethylene, $R_{22}$ is methylene, $R_{23}$ is methylene, $R_{24}$ is hydrogen or

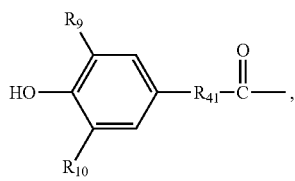

$R_{30}$ is methylene, $R_{31}$ is $C_8$-$C_{13}$alkyl, $R_{41}$ is ethylene, m is 0, 1 or 2, n is 0 or 1, and p is 1 or 2.

As already mentioned, the compounds of formula I are preferably prepared, for example, by oxidation of the corresponding sulfides using peroxides. Many of those sulfides are not described in the literature.

The present invention accordingly relates also to compounds of formula Ia

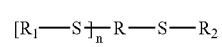

(Ia)

wherein, when n is 0,

R is $C_1$-$C_{25}$alkyl, $C_2$-$C_{18}$hydroxyalkyl,

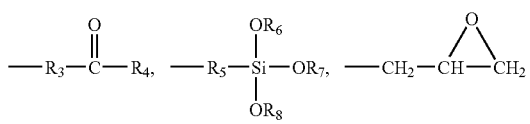

or a radical of formula II, III, IV, V, VI, VII, VIII or IX

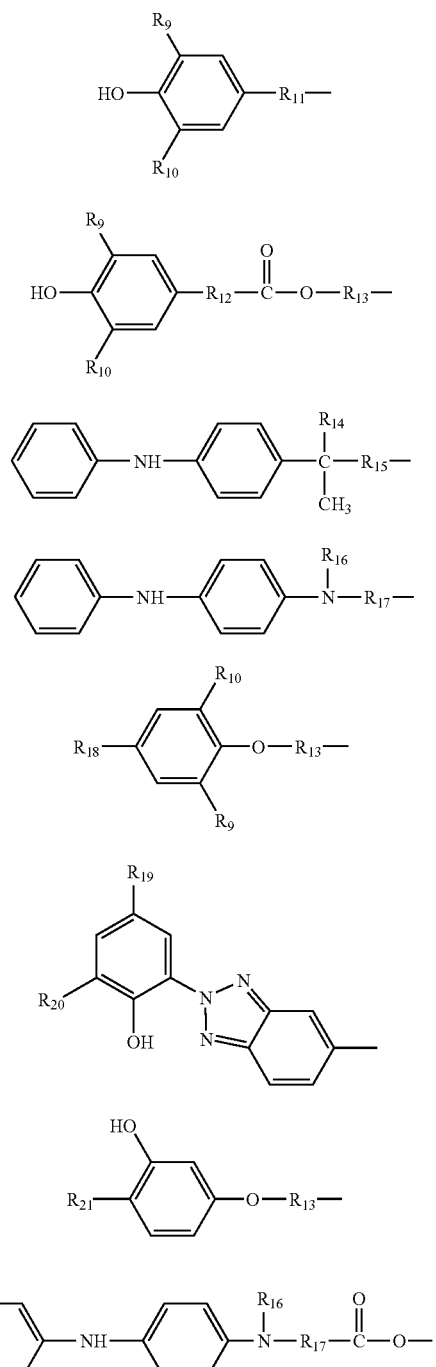

when n is 1,
R is $C_1$-$C_{18}$alkylene,

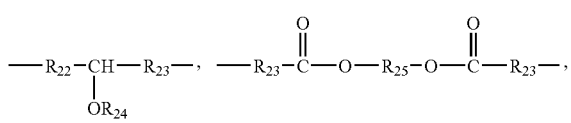

-continued

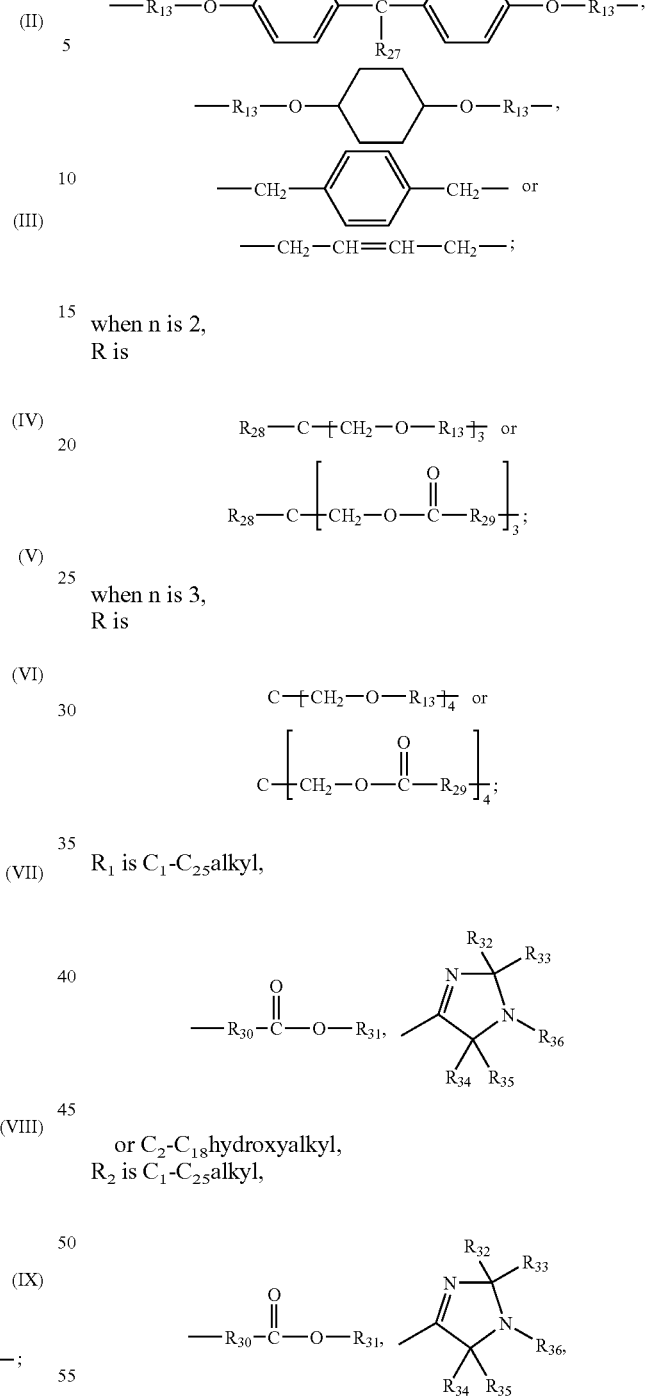

when n is 2,
R is when n is 3,
R is $R_1$ is $C_1$-$C_{25}$alkyl, or $C_2$-$C_{18}$hydroxyalkyl,
$R_2$ is $C_1$-$C_{25}$alkyl, $C_2$-$C_{18}$hydroxyalkyl or a radical of formula III or IX,
$R_3$ is $C_1$-$C_{18}$alkylene, or $C_2$-$C_{18}$alkylene interrupted by oxygen or by sulfur,
$R_4$ is hydroxy, $C_1$-$C_{18}$alkoxy, or $C_3$-$C_{18}$alkoxy interrupted by oxygen or by sulfur,
$R_5$ is $C_1$-$C_{12}$alkylene, or $C_2$-$C_{12}$alkylene interrupted by oxygen,
$R_6$, $R_7$ and $R_8$ are each independently of the others hydrogen, $C_1$-$C_{12}$alkyl, $C_2$-$C_{12}$alkyl interrupted by oxygen or by sulfur; or $C_3$-$C_{12}$alkenyl, $R_9$ is hydrogen, $C_1$-$C_8$alkyl, $C_5$-$C_8$cycloalkyl, $C_7$-$C_9$phenylalkyl or phenyl, $R_{10}$ is $C_1$-$C_8$alkyl, $C_5$-$C_8$cycloalkyl, $C_7$-$C_9$phenylalkyl, phenyl,

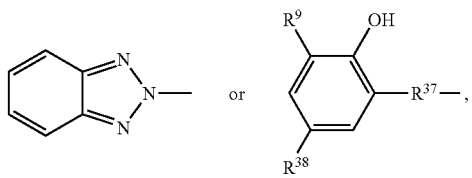

$R_{11}$ is a direct bond or unsubstituted or $C_1$-$C_4$alkyl-substituted $C_1$-$C_8$alkylene, $R_{12}$ is a direct bond or unsubstituted or $C_1$-$C_4$alkyl-substituted $C_1$-$C_8$alkylene, $R_{13}$ is $C_1$-$C_8$alkylene or

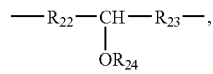

$R_{14}$ is hydrogen or $C_1$-$C_4$alkyl, $R_{15}$ is $C_1$-$C_4$alkylene, $R_{16}$ is hydrogen, cyclohexyl or $C_3$-$C_{12}$alkyl, $R_{17}$ is $C_1$-$C_8$alkylene or

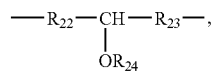

$R_{18}$ is hydrogen, $C_1$-$C_{12}$alkyl or a radical of formula II, $R_{19}$ is $C_1$-$C_{12}$alkyl or $C_7$-$C_9$phenylalkyl, $R_{20}$ is $C_1$-$C_{12}$alkyl or $C_7$-$C_9$phenylalkyl, $R_{21}$ is

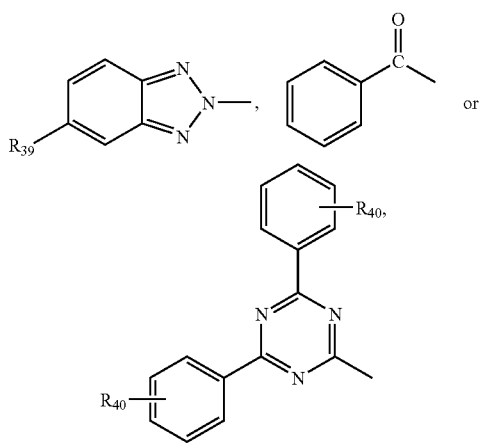

$R_{22}$ is a direct bond or $C_1$-$C_8$alkylene, $R_{23}$ is $C_1$-$C_8$alkylene, $R_{24}$ is hydrogen, $C_1$-$C_{25}$alkyl, $C_2$-$C_{25}$alkanoyl,

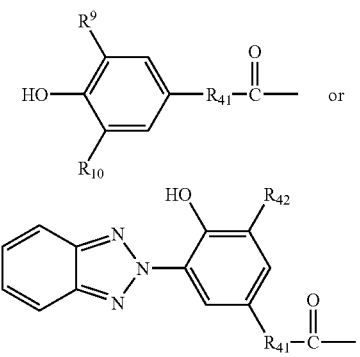

$R_{25}$ is $C_2$-$C_{18}$alkylene or $C_2$-$C_{18}$alkylene interrupted by oxygen or by sulfur, $R_{26}$ and $R_{27}$ are each independently of the other hydrogen, $CF_3$, $C_1$-$C_{12}$alkyl or phenyl, or $R_{26}$ and $R_{27}$, together with the carbon atom to which they are bonded, form a $C_5$-$C_8$cycloalkylidene ring that is unsubstituted or substituted by from 1 to 3 $C_1$-$C_4$alkyl groups, $R_{28}$ is $C_1$-$C_8$alkyl, $R_{29}$ is $C_1$-$C_{12}$alkylene, $R_{30}$ is $C_1$-$C_8$alkylene, $R_{31}$ is $C_1$-$C_{25}$alkyl, $R_{32}$, $R_{33}$, $R_{34}$ and $R_{35}$ are each independently of the others $C_1$-$C_8$alkyl; or the radicals $R_{32}$ and $R_{33}$ or the radicals $R_{34}$ and $R_{35}$, together with the carbon atom to which they are bonded, form a $C_5$-$C_{12}$cycloalkylidene ring, $R_{36}$ is hydrogen, $C_1$-$C_{18}$alkyl, $C_3$-$C_6$alkenyl, $C_3$-$C_6$alkynyl, $C_7$-$C_{12}$phenylalkyl, $C_1$-$C_8$acyl, $C_1$-$C_{18}$alkoxy, $C_1$-$C_{18}$hydroxyalkoxy, $C_2$-$C_{18}$alkenyloxy or $C_5$-$C_{12}$cycloalkoxy, $R_{37}$ is $C_1$-$C_4$alkylene, sulfur or $C_2$-$C_8$alkylidene, $R_{38}$ is hydrogen, $C_1$-$C_8$alkyl, $C_5$-$C_8$cycloalkyl or phenyl, $R_{39}$ is hydrogen, halogen, —SO—$C_1$-$C_{25}$alkyl or —$SO_2$—$C_1$-$C_{25}$alkyl, $R_{40}$ is hydrogen, $C_1$-$C_8$alkyl or phenyl, $R_{41}$ is a direct bond, or unsubstituted or $C_1$-$C_4$alkyl-substituted $C_1$-$C_8$alkylene, $R_{42}$ is hydrogen, $C_1$-$C_8$alkyl, $C_5$-$C_8$cycloalkyl or $C_7$-$C_9$phenylalkyl, n is 0, 1, 2 or 3, with the proviso that, when n is 0, R is a radical of formula V, $R_{17}$ is

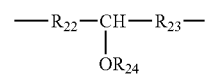

and $R_{22}$ and $R_{23}$ are methylene, then $R_{24}$ is other than hydrogen.

Preferred groups of novel compounds of formula Ia correspond to the preferences expressed hereinbefore for polymer grafting.

Of special interest are compounds of formula Ia wherein, when n is 0,

R is $C_1$-$C_{12}$alkyl, $C_2$-$C_8$hydroxyalkyl,

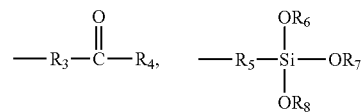

or a radical of formula II, III, IV, V, VI, VII, VIII or IX;
when n is 1,
R is $C_1$-$C_8$alkylene,

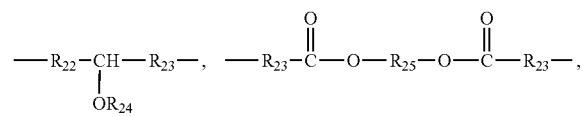

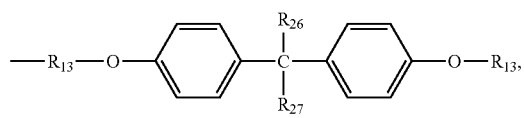

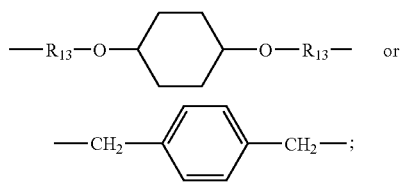

when n is 2,
R is

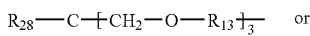

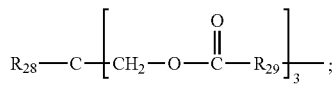

when n is 3,
R is

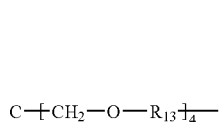

$R_1$ is $C_4$-$C_{18}$alkyl,

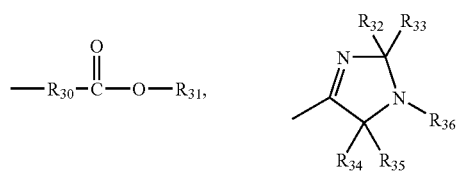

or $C_2$-$C_8$hydroxyalkyl,
$R_2$ is $C_4$-$C_{18}$alkyl,

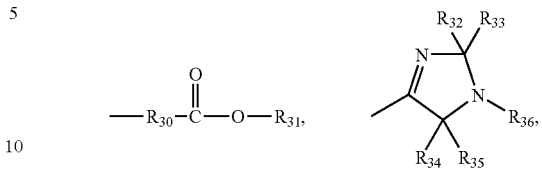

$C_2$-$C_8$hydroxyalkyl or a radical of formula III or IX,
$R_3$ is $C_1$-$C_8$alkylene,
$R_4$ is $C_1$-$C_8$alkoxy,
$R_5$ is $C_1$-$C_8$alkylene,
$R_6$, $R_7$ and $R_8$ are each independently of the others hydrogen, $C_1$-$C_8$alkyl or $C_3$-$C_8$alkenyl,
$R_9$ is $C_1$-$C_8$alkyl, cyclohexyl or $C_7$-$C_9$phenylalkyl,
$R_{10}$ is $C_1$-$C_8$alkyl, cyclohexyl, $C_7$-$C_9$phenylalkyl,

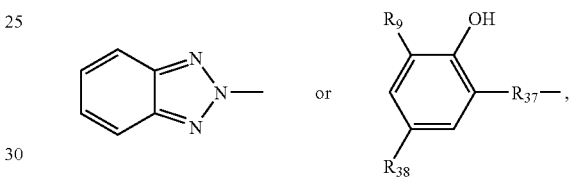

$R_{11}$ is $C_1$-$C_8$alkylene,
$R_{12}$ is $C_1$-$C_8$alkylene,
$R_{13}$ is $C_1$-$C_8$alkylene or

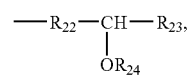

$R_{14}$ is $C_1$-$C_4$alkyl,
$R_{15}$ is $C_1$-$C_4$alkylene,
$R_{16}$ is $C_3$-$C_8$alkyl,
$R_{17}$ is $C_1$-$C_8$alkylene or

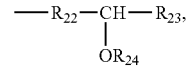

$R_{18}$ is hydrogen or $C_1$-$C_8$alkyl,
$R_{19}$ is $C_1$-$C_8$alkyl or $C_7$-$C_9$phenylalkyl,
$R_{20}$ is $C_1$-$C_8$alkyl or $C_7$-$C_9$phenylalkyl,
$R_{21}$ is

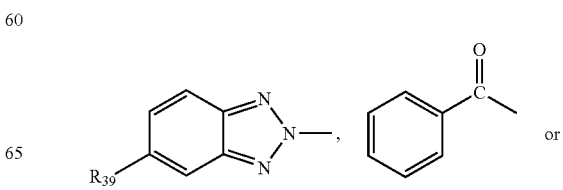

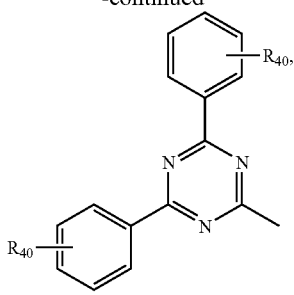

$R_{22}$ is $C_1$-$C_6$alkylene,
$R_{23}$ is $C_1$-$C_6$alkylene,
$R_{24}$ is hydrogen, $C_1$-$C_{12}$alkyl, $C_2$-$C_{12}$alkanoyl,

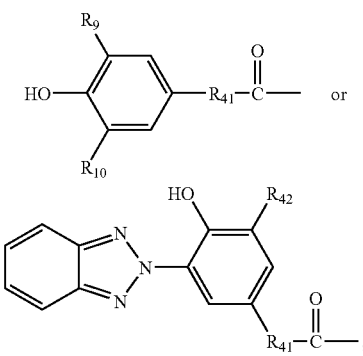

$R_{25}$ is $C_2$-$C_8$alkylene,
$R_{26}$ and $R_{27}$ are each independently of the other hydrogen or $C_1$-$C_4$alkyl, or $R_{26}$ and $R_{27}$, together with the carbon atom to which they are bonded, form a cyclohexylidene ring,
$R_{28}$ is $C_1$-$C_4$alkyl,
$R_{29}$ is $C_1$-$C_4$alkylene,
$R_{30}$ is $C_1$-$C_4$alkylene,
$R_{31}$ is $C_4$-$C_{18}$alkyl,
$R_{32}$, $R_{33}$, $R_{34}$ and $R_{35}$ are each independently of the others $C_1$-$C_4$alkyl; or the radicals $R_{32}$ and $R_{33}$ or the radicals $R_{34}$ and $R_{35}$, together with the carbon atom to which they are bonded, form a cyclohexylidene ring,
$R_{36}$ is hydrogen, $C_1$-$C_8$alkyl, benzyl, $C_1$-$C_8$acyl, $C_1$-$C_8$alkoxy, $C_2$-$C_8$hydroxyalkoxy, $C_3$-$C_8$-alkenyloxy or cyclohexyloxy,
$R_{37}$ is $C_1$-$C_4$alkylene or $C_2$-$C_4$alkylidene,
$R_{38}$ is hydrogen, $C_1$-$C_4$alkyl or cyclohexyl,
$R_{39}$ is hydrogen, chlorine, —SO—$C_1$-$C_{12}$alkyl or —SO$_2$—$C_1$-$C_{12}$alkyl,
$R_{40}$ is hydrogen or $C_1$-$C_4$alkyl,
$R_{41}$ is $C_1$-$C_8$alkylene,
$R_{42}$ is $C_1$-$C_8$alkyl, cyclohexyl or $C_7$-$C_9$phenylalkyl, and
n is 0, 1, 2 or 3.

Because of their lack of a sulfoxide or sulfone group, the compounds of formula Ia are not suitable for polymer grafting. However, it has been found, surprisingly, that the compounds of formula Ia are highly suitable as stabilisers for organic materials against oxidative, thermal, dynamic, light-induced and/or ozone-induced degradation.

The present invention accordingly relates also to compositions comprising
a) an organic material subject to oxidative, thermal, dynamic, light-induced and/or ozone-induced degradation, and
b) at least one compound of formula Ia.

Preferred organic materials are the same as the polymers mentioned hereinbefore under sections 1. to 31.

The compounds of formula Ia are added to the organic material in an amount of, advantageously, from 0.05 to 10%, for example from 0.1 to 5%, preferably from 0.5 to 3.0%, based on the weight of the organic material.

The organic materials may likewise additionally comprise further additives, for example the list of co-stabilisers mentioned hereinbefore (antioxidants, UV absorbers and light stabilisers, metal deactivators, phosphites and phosphonites, benzofuranones, hydroxylamines, nitrones, thiosynergistic compounds, peroxide-destroying compounds, polyamide stabilisers, basic co-stabilisers, nucleating agents, fillers and reinforcing agents, plasticisers, lubricants, emulsifiers, pigments, rheology additives, catalysts, flow improvers, optical brighteners, flame retardants, antistatics or blowing agents).

The compounds of formula Ia are prepared preferably by ring-opening of epoxides using mercaptene. Some of those epoxides are not described in the literature.

The present invention accordingly relates also to novel compounds of formulae A, A2, A3 and A4

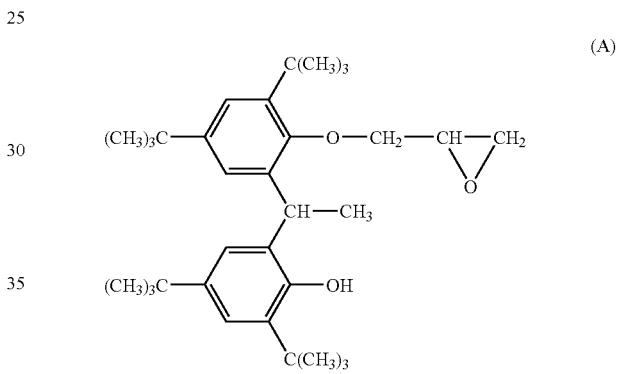

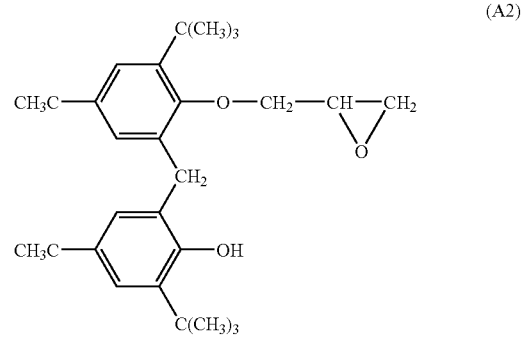

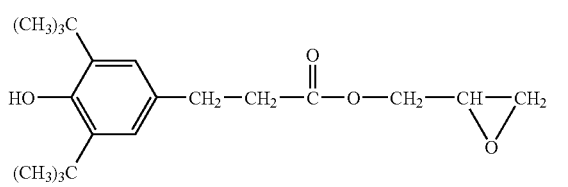

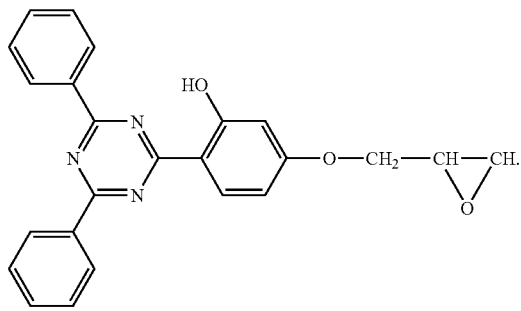

(A4)

The compounds of formulae A, A2, A3 and A4 are prepared, for example, as disclosed in the experimental section, preferably by reacting the corresponding phenols with epichlorohydrin or epibromohydrin.

The present invention relates also to a method of stabilising polymers against oxidative, thermal, dynamic, light-induced and/or ozone-induced degradation, which method comprises grafting those polymers with at least a compound of formula I.

The present invention relates also to a method of grafting compounds of formula I onto polymers, which method comprises heating, in a processing apparatus for polymers, a mixture of polymer and at least one compound of formula I above the softening point of the polymer and allowing them to react with one another.

A further embodiment of the present invention is the use of compounds of formula I as stabilisers for polymers against oxidative, thermal, dynamic, light-induced and/or ozone-induced degradation.

A further embodiment of the present invention is the use of compounds of formula I as grafting agents for polymers.

Preferred compounds of formula I for the above-mentioned methods and uses are the same as the preferences expressed hereinbefore for polymer grafting.

The following Examples further illustrate the invention. Parts or percentages relate to weight.

EXAMPLE 1

Preparation of 1-tert-nonylthio-3-tert-nonylsulfinyl-2-propyl-3,5-di-tert-butyl-4-hydroxyphenyl propionate (Compound 101)

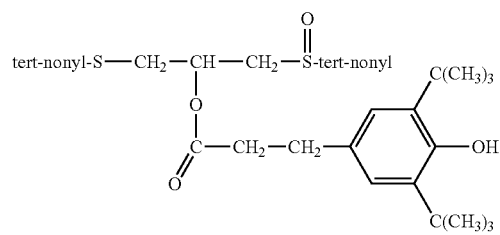

To 23.3 g (0.036 mol) of 1,3-bis(tert-nonylthio)-2-propyl-3,5-di-tert-butyl-4-hydroxyphenyl propionate [prepared in analogy to U.S. Pat. No. 3,954,839 from 1,3-bis(tert-nonylthio)-2-propanol and 3,5-di-tert-butyl-4-hydroxyphenyl-propionic acid chloride] in 40 ml of acetone there are added, dropwise, at room temperature, 7.3 g (0.073 mol) of 35% aqueous hydrogen peroxide solution. The reaction mixture is stirred for 24 hours at room temperature; it is then diluted with water and the acetone is removed using a vacuum rotary evaporator. The aqueous residue is extracted with ethyl acetate. The organic phase is separated off, dried over sodium sulfate and concentrated using the vacuum rotary evaporator. Chromatography of the oily residue on silica gel using the mobile phase ethyl acetate/hexane=1:5 yields the compound (101) in the form of a yellowish oil having an $R_F$ (ethyl acetate/hexane =1:5) of 0.27. MS [chemical ionisation (CI)]: 653 ($MH^{3O}$).

In analogy to Example 1, using 1,3-bis(tert-dodecylthio)-2-propyl-3,5-di-tert-butyl-4-hydroxy-phenyl propionate instead of 1,3-bis(tert-nonylthio)-2-propyl-3,5-di-tert-butyl-4-hydroxyphenyl propionate, the compound (102) is obtained in the form of a yellowish oil having an $R_F$(ethyl acetate/hexane=1:5) of 0.27. MS (CI): 737 ($MH^{3O}$).

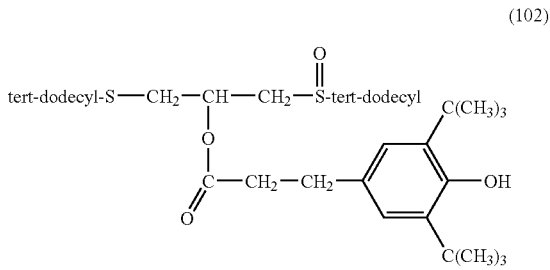

EXAMPLE 2

Preparation of 1-isooctyloxycarbonylmethylthio-3-isooctyloxycarbonylmethyl-sulfinyl-2-propyl-3,5-di-tert-butyl-4-hydroxyphenyl propionate (Compound 103)

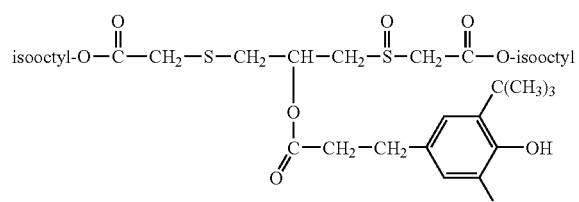

In analogy to Example 1, 1,3-bis(isooctyloxycarbonylmethylthio)-2-propyl-3,5-di-tert-butyl-4-hydroxyphenyl propionate instead of 1,3-bis(tert-nonylthio)-2-propyl-3,5-di-tert-butyl4-hydroxyphenyl propionate is stirred with 35% aqueous hydrogen peroxide solution for 12 hours at 45° C. The reaction mixture is worked up in analogy to Example 1. Chromatography of the residue on silica gel using the mobile phase hexane/acetone=3:2 yields the compound (103) in the form of a yellowish oil having an $R_F$ (hexane/acetone=3:2) of 0.54. MS (Cl): 740 (MH$^{30}$).

EXAMPLE 3

Preparation of 1-n-octylthio-3-n-octylsulfinyl-2-propyl-3,5-di-tert-butyl-4-hydroxyphenyl propionate (Compound 104)

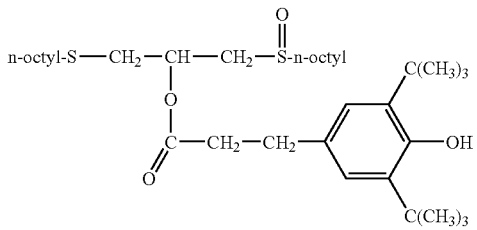
(104)

To 6.1 g (0.01 mol) of 1,3-bis(n-octylthio)-2-propyl-3,5-di-tert-butyl4-hydroxyphenyl propionate [prepared in analogy to U.S. Pat. No. 3,954,839 from 1,3-bis(n-octylthio)-2-propanol and 3,5-di-tert-butyl4-hydroxyphenylpropionic acid methyl ester by transesterification in the presence of 0.5% Fascat 4200 (RTM)] in 10 ml of acetone there added, dropwise, at room temperature, 2.0 g (0.02 mol) of 35% aqueous hydrogen peroxide solution. The reaction mixture is stirred for 8 hours at 45° C., cooled to room temperature and diluted with water; the acetone is removed using a vacuum rotary evaporator. The aqueous residue is extracted with ethyl acetate. The organic phase is separated off, dried over sodium sulfate and concentrated using the vacuum rotary evaporator. Chromatography of the oily residue on silica gel using the mobile phase ethyl acetate/hexane=1:1 yields the compound (104) in the form of a yellowish oil having an $R_F$ (ethyl acetate/hexane=1:1) of 0.65. MS (Cl): 624 (MH$^+$).

EXAMPLE 4

Preparation of 3,5-di-tert-butyl-4-hydroxybenzyl-tert-nonyl sulfoxide (compound 105)

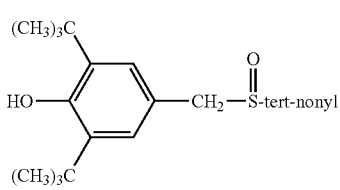
(105)

In analogy to Example 1, using 2,6-di-tert-butyl-4-(tert-nonylthiomethyl)phenol instead of 1,3-bis(tert-nonylthio)-2-propyl-3,5-di-tert-butyl-4-hydroxyphenyl propionate, the compound (105) is obtained in the form of a yellowish oil having an $R_F$ (dichloromethane/ethyl acetate=19:1)of 0.31.

EXAMPLE 5

Preparation of 3-thia-3-oxo-pentane-1,5-diyl-bis[3-(3,5-di-tert-butyl-4-hydroxyphenyl)propionate] (Compound 106)

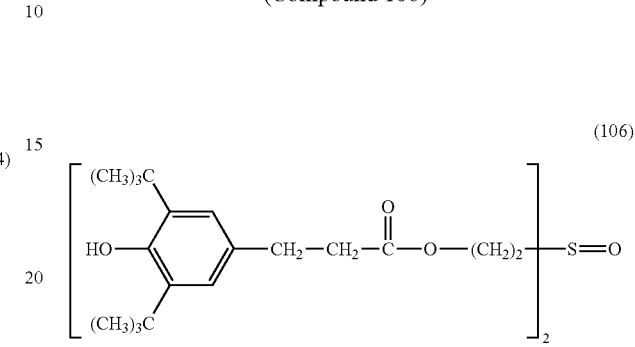
(106)

To a solution of 6.4 g (0.01 mol) of 3-thiapentane-1,5-diyl-bis[3-(3,5-di-tert-butyl-4-hydroxyphenyl)propionate] [Irganox 1035 (RTM), Ciba SC] in 40 ml of acetic acid there are added 1.7 g (0.01 mol) of 3-chloroperbenzoic acid. After stirring for 4 hours at room temperature, a further 0.85 g (0.005 mol) of 3-chloroperbenzoic acid is added and stirring is then carried out for a further 4 hours at room temperature. The reaction mixture is poured onto water and extracted with diethyl ether. The organic phase is washed with water, dried over sodium sulfate and concentrated using a vacuum rotary evaporator. Crystallisation of the residue from hexane yields the compound (106), m.p. 92-94° C., having an $R_F$ (chloroform/methanol=49:1) of 0.61. MS (Cl): 659 (MH$^{30}$).

EXAMPLE 6

Preparation of 1,3-bis(tert-dodecylsulfinyl)-2-propanol (Compound 107)

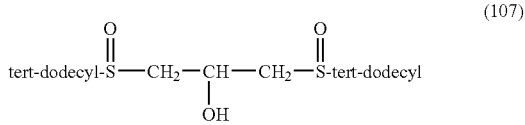
(107)

To a solution of 18.4 g (0.04 mol) of 1,3-bis(tert-dodecylthio)-2-propanol in 20 ml of acetone there are added, dropwise, at about 5° C., 8 g (0.08 mol) of a 35% aqueous solution of hydrogen peroxide. The reaction mixture is stirred for 24 hours at room temperature and is then diluted with water; the acetone is removed using a vacuum rotary evaporator. The aqueous residue is extracted with ethyl acetate. The organic phase is separated off, dried over sodium sulfate and concentrated using the vacuum rotary evaporator. Chromatography of the oily residue on silica gel using the mobile phase ethyl acetate/hexane=1:1 yields the compound (107) in the form of a yellowish oil having an $R_F$ (ethyl acetate) of 0.43. MS (Cl): 493 (MH$^{3o}$).

EXAMPLE 7

Preparation of 1-tert-dodecylsulfinyl-3-tert-dodecyl-sulfonyl-2-propanol (Compound 108)

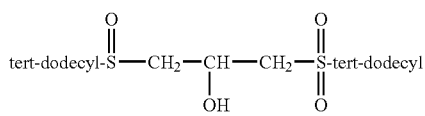
(108)

To a solution of 46.0 g (0.10 mol) of 1,3-bis(tert-dodecylthio)-2-propanol in 50 ml of acetone there are added, dropwise, at room temperature, 40 g (0.40 mol) of a 35% aqueous solution of hydrogen peroxide. The reaction mixture is stirred for 24 hours at 50° C. and is then diluted with water; the acetone is removed using a vacuum rotary evaporator. The aqueous residue is extracted with ethyl acetate. The organic phase is separated off, dried over sodium sulfate and concentrated using the vacuum rotary evaporator. Chromatography of the oily residue on silica gel using the mobile phase ethyl acetate/hexane=1:1 yields the compound (108) in the form of a yellowish oil having an $R_F$ (ethyl acetate/hexane=1:1) of 0.10. MS (Cl): 509 (MH$^{3o}$).

EXAMPLE 8

Preparation of 1,3-bis(tert-dodecylsulfonyl)-2-propanol (Compound 109)

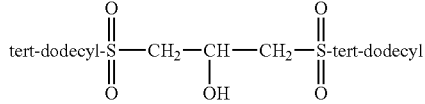
(109)

The compound (109) is obtained, on preparation of compound (108) according to Example 7, in further chromatography fractions in the form of a yellowish oil having an $R_F$ (ethyl acetate/hexane=1:1) of 0.44. MS (Cl): 525 (MH$^{3o}$).

EXAMPLE 9

Preparation of 1,3-bis(n-octylsulfinyl)-2-propyl-3,5-di-tert-butyl4-hydroxyphenyl propionate (Compound 110)

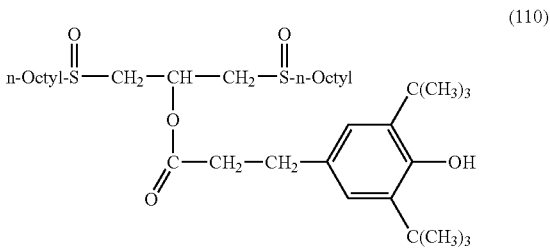
(110)

To 6.1 g (0.01 mol) of 1,3-bis(n-octylthio)-2-propyl-3,5-di-tert-butyl-4-hydroxyphenyl propionate [prepared in analogy to U.S. Pat. No. 3,954,839 from 1,3-bis(n-octylthio)-2-propanol and 3,5-di-tert-butyl-4-hydroxyphenylpropionic acid methyl ester by transesterification in the presence of 0.5% Fascat 4200 (RTM)] in 10 ml of acetone there are added, dropwise, at room temperature, 4.0 g (0.04 mol) of 35% aqueous hydrogen peroxide solution. The reaction mixture is stirred for 8 hours at 45° C., cooled to room temperature and diluted with water; the acetone is removed using a vacuum rotary evaporator. The aqueous residue is extracted with ethyl acetate. The organic phase is separated off, dried over sodium sulfate and concentrated using the vacuum rotary evaporator. Chromatography of the oily residue on silica gel using the mobile phase ethyl acetate/hexane=1:1 yields the compound (110), m.p. 95-99° C. MS (Cl): 640 (MH$^{3o}$).

EXAMPLE 10

Preparation of 1,3-bis(isooctyloxycarbonylmethyl-sulfinyl)-2-propyl-3,5-di-tert-butyl-4-hydroxyphenyl propionate (Compound 111)

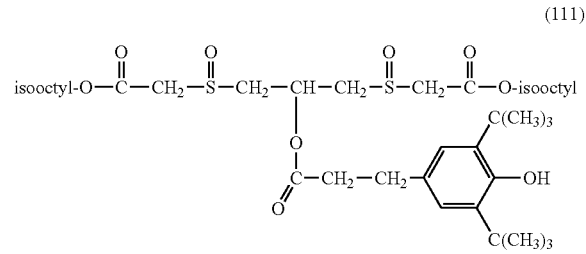
(111)

In analogy to Example 9, 1,3-bis(isooctyloxycarbonylmethylthio)-2-propyl-3,5-di-tert-butyl-4-hydroxyphenyl propionate instead of 1,3-bis(n-octylthio)-2-propyl-3,5-di-tert-butyl-4-hydroxyphenyl propionate is stirred with 35% aqueous hydrogen peroxide solution for 12 hours at 45° C. The reaction mixture is worked up in analogy to Example 9. Chromatography of the residue on silica gel using the mobile phase hexane/acetone=3:2 yields the compound (111) in the form of a colourless resin having an $R_F$ (hexane/acetone=3:2) of 0.32. MS (Cl): 756 (MH$^{30}$).

EXAMPLE 11

Preparation of 1-tert-dodecylsulfinyl-3-[2,4-di-tert-butyl-6-(3,5-di-tert-butyl-2-hydroxy-α-methylbenzyl)phenyloxy]-2-propanol (Compound 112)

a) Preparation of the Epoxide of Formula A.

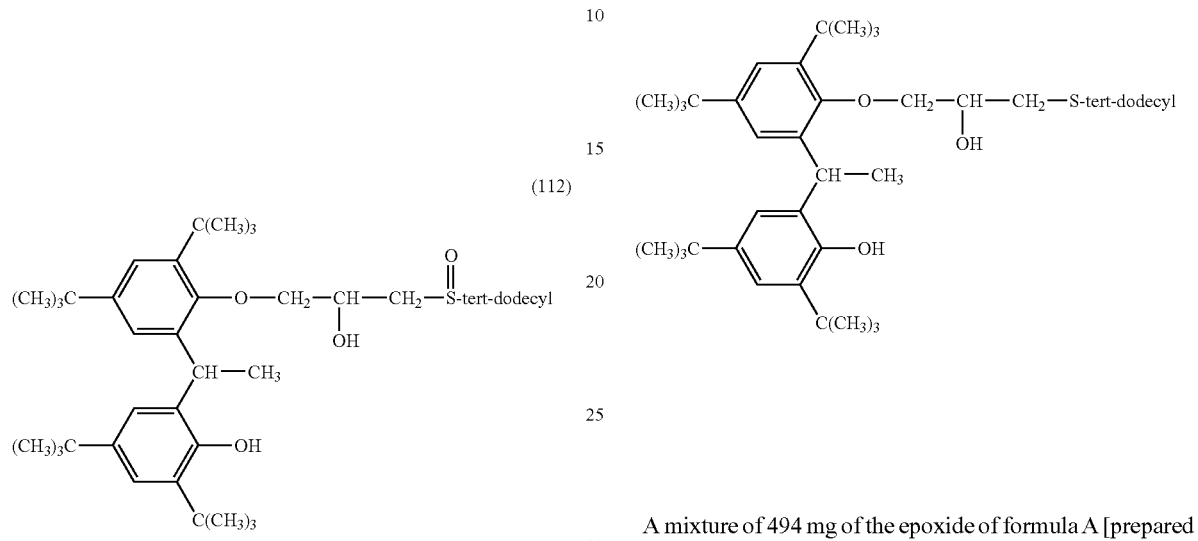

To 131.6 g of 2,2-ethylidene-bis-4,6-di-tert-butylphenol and 300 ml of epichlorohydrin there are added, at 25° C., over the course of 2 hours, 33.7 g of potassium tert-butylate, and the mixture is maintained at 60° C. for 4 hours. After extracting the reaction mixture with water/toluene, isolating the organic phase and concentrating by evaporating off the solvent, 98.7 g (67%) of the compound of formula A are obtained in the form of a colourless powder, m.p. 133° C.

b) Preparation of the Compound of Formula B.

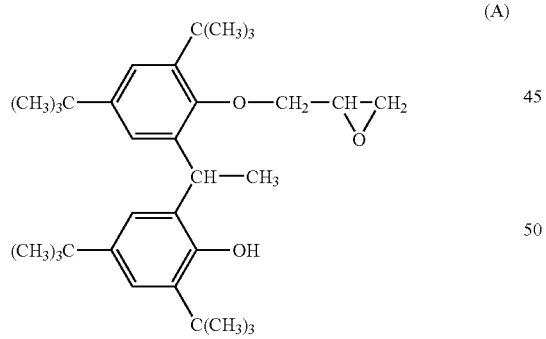

A mixture of 494 mg of the epoxide of formula A [prepared according to Example 11a], 242 mg of tert-dodecylmercaptan (isomeric mixture) and 1.66 g of potassium carbonate in 3 ml of dimethylformamide is stirred for 8 hours at 110° C. Extraction with hexane and customary working-up of the organic phase yields, after isolation and drying, 0.56 g (80%) of the compound of formula B, yellowish oil, MS(EI): 696 (M$^{30}$).

In analogy to Example 11 b, using n-dodecylmercaptan instead of tert-dodecylmercaptan, the compound of formula B2, m.p. 90° C., is obtained. MS(EI):683 (M$^{30}$).

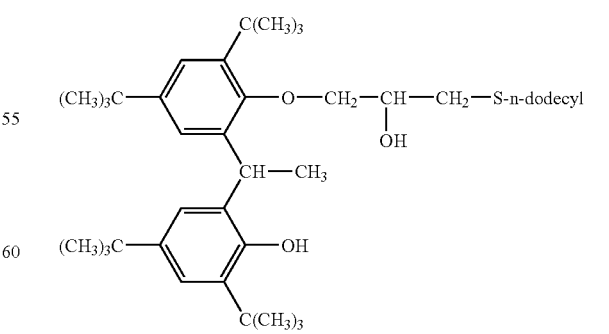

c) Preparation of the Compound 112.

16.8 g of the compound of formula B [prepared according to Example 11b] are dissolved in 50 ml of acetone, and 4.7 g of 35% aqueous hydrogen peroxide are added; the mixture is stirred for 36 hours at 45° C. Water is then added to the reaction mixture. The product is extracted with ethyl acetate. After customary working-up, 15.4 g (90%) of the compound 112, white powder, m.p. 72° C., are obtained. MS(Cl): 713 (MH$^{30}$).

In analogy to Example 11c, using the compound of formula B2 instead of the compound of formula B, the compound 113, m.p. 198° C., is obtained. MS(Cl): 713 (MH$^{30}$).

(113)

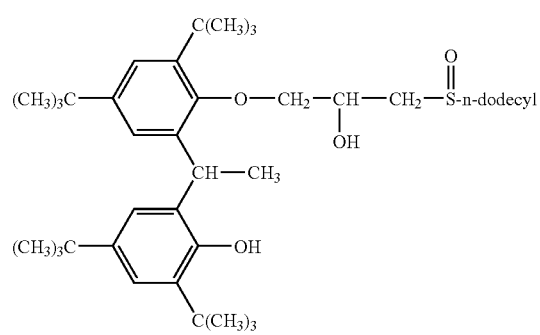

In analogy to Example 11b and 11c, the compounds B3 to B9 and 114 to 120 are prepared using the epoxide A2

(A2)

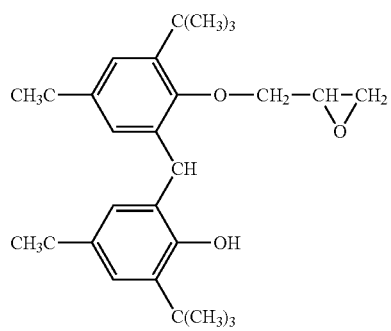

instead of the epoxide A. The results are compiled in Table 1

TABLE 1

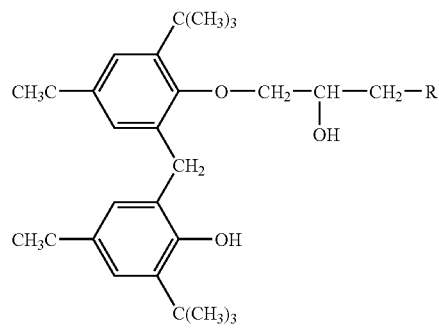

| Compound | R | m.p. (° C.) |
|---|---|---|
| B3 | —S-n-dodecyl | 60 |
| B4 | —S-tert-dodecyl | oil |
| B5 | —S-n-octyl | yellow resin |
| B6 | —S-tert-nonyl | yellow resin |
| B7 | —S-n-octadecyl | 70 |
| B8 | —S—CH$_2$—CO$_2$-isooctyl | yellow oil |
| B9 | —S—CH$_2$CH$_2$—CO$_2$-isooctyl | brown oil |
| 114 | —S(O)-n-dodecyl | 105 |
| 115 | —S(O)-tert-dodecyl | yellow resin |
| 116 | —S(O)-n-octyl | yellow resin |
| 117 | —S(O)-tert-nonyl | yellow resin |
| 118 | —S(O)-n-octadecyl | 94-96 |
| 119 | —S(O)—CH$_2$—CO$_2$-isooctyl | yellow resin |
| 120 | —S(O)—CH$_2$CH$_2$—CO$_2$-isooctyl | yellow oil |

In analogy to Example 11b and 11c, the compounds B10 to B13 and 121 to 124 are prepared using the epoxide A3

(A3)

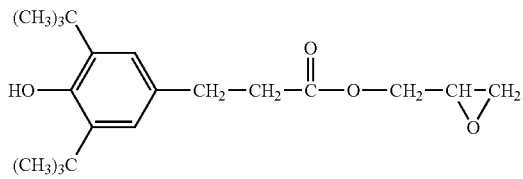

instead of the epoxide. The results are compiled in Table 2.

TABLE 2

| Compound | R | m.p. (° C.) |
|---|---|---|
| B10 | —S-n-dodecyl | orange oil |
| B11 | —S-tert-dodecyl | oil |
| B12 | —S—CH$_2$—CO$_2$-isooctyl | yellow oil |
| B13 | —S—CH$_2$CH$_2$—CO$_2$-isooctyl | yellow oil |
| 121 | —S(O)-n-dodecyl | yellow oil |
| 122 | —S(O)-tert-dodecyl | yellow oil |
| 123 | —S(O)—CH$_2$—CO$_2$-isoooctyl | orange oil |
| 124 | —S(O)—CH$_2$CH$_2$—CO$_2$-isooctyl | yellow oil |

EXAMPLE 12

Preparation of the Compounds B14, B15, 125 and 126 (Table 3)

TABLE 3

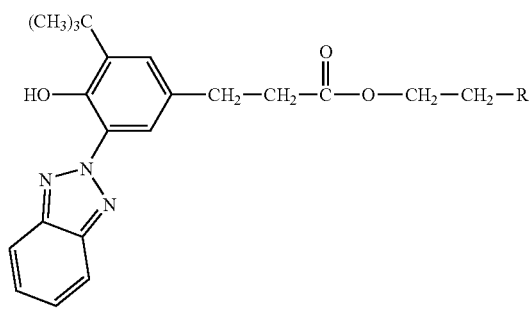

| Compound | R | m.p. (° C.) |
|---|---|---|
| B14 | —S-n-dodecyl | colourless oil |
| B15 | —S-tert-dodecyl | yellow oil |
| 125 | —S(O)-n-dodecyl | 61 |
| 126 | —S(O)-tert-dodecyl | yellow resin |

37.36 g of 3-[3-(2-benzotriazolyl)-5-tert-butyl-4-hydroxyphenyl]propionic acid methyl ester, 26.05 g of 2-n-dodecylthioethanol and 0.19 g of Fascat 4200 are maintained at 165° C. for 24 hours. The reaction mixture is cooled and chromatographed on silica gel using the mobile phase system (hexane/ethyl acetate=19:1), resulting in 56.25 g (94%) of the compound B14 (Table 3), colourless oil, MS (El):267 ($M^{3O}$).

50 g of the compound B14 (Table 3) are dissolved in 50 ml of acetone and oxidised using 17.13 g of 35% aqueous hydrogen peroxide solution according to customary procedure at 45° C. to form the sulfoxide, resulting in 52 g (100%) of the compound 125 (Table 3), m.p. 61° C., MS (Cl) 584 ($MH^{3O}$).

In analogous manner, the compounds B15 and 126 (Table 3) are obtained using 2-tert-dodecylthioethanol instead of 2-n-dodecylthioethanol.

EXAMPLE 13

Preparation of the Compounds B16, 127 and 128 (Table 4)

TABLE 4

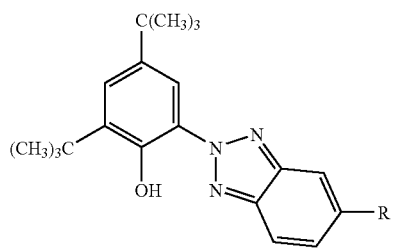

| Compound | $R^1$ | $R^2$ | m.p. (° C.) |
|---|---|---|---|
| B16 | —S-n-octyl | —S-n-octyl | 52 |
| 127 | —S(O)-n-octyl | —S-n-octyl | 124[a] |
| 128 | —S(O)-n-octyl | —S(O)-n-octyl | 124[a] |

[a] mixture of compounds 127 and 128

30 g of 3-[3-(benzotriazolyl)-5-tert-butyl-4-hydroxyphenyl]propionic acid methyl ester, 29.6 g of 1,3-dioctylthio-2-propanol and 0.15 g of Fascat 4200 are maintained at 170-175° C. for 20 hours. The reaction mixture is cooled and chromatographed on silica gel using the mobile phase system hexane/ethyl acetate=4:1, resulting in 40.55 g (71%) of the compound B16 (Table 4), m.p. 52° C., MS (Cl): 670 ($MH^{3O}$).

30 g of the compound B16 (Table 4) are dissolved in 40 ml of acetone and oxidised using 8.71 g of 35% aqueous hydrogen peroxide solution according to customary procedure for 2 hours at 45° C. to form the sulfoxide, resulting in a mixture of the compounds 127 and 128 (Table 4), which are not separated chromatographically. Yield 100%, m.p. 124° C., MS (Cl): 702 and 686 ($MH^{3O}$).

EXAMPLE 14

Preparation of the Compounds B17-B19 and 129-131 (Table 5)

TABLE 5

| Compound | R | m.p. (° C.) |
|---|---|---|
| B17 | —S-n-dodecyl | 63 |
| B18 | —S-tert-dodecyl | yellow oil |
| B19 | —S—$CH_2CH_2$—$CO_2$-isooctyl | yellow oil |
| 129 | —S(O)-n-dodecyl | yellow oil |
| 130 | —S(O)-tert-dodecyl | yellow resin |
| 131 | —S(O)—$CH_2CH_2$—$CO_2$-isooctyl | yellow resin |

Preparation of the compounds according to Table 5 is carried out in analogy to the procedure described in U.S. 6,040,455.

EXAMPLE 15

Preparation of the Compounds B20-B30 and 132-142 (Table 6)

TABLE 6

[Structure: phenyl-NH-phenyl-N(R16)-CH2-CH2-CH2-R]

| Compound | $R_{16}$ | R | m.p (° C.) |
|---|---|---|---|
| B20 | isopropyl | —S-n-dodecyl | 56 |
| B21 | isopropyl | —S-tert-dodecyl | light-brown oil |
| B22 | isopropyl | —S—CH$_2$CH$_2$—CO$_2$-isooctyl | dark oil |
| B23 | isopropyl | —S—CH$_2$—CO$_2$-isooctyl | dark oil |
| B24 | isopropyl | —S-n-octadecyl | |
| B25 | 1,3-dimethylbutyl | —S-tert-dodecyl | |
| B26 | 1,3-dimethylbutyl | —S-n-dodecyl | |
| B27 | 1,3-dimethylbutyl | —S—CH$_2$CH$_2$—CO$_2$-isooctyl | |
| B28 | 1,3-dimethylbutyl | —S—CH$_2$—CO$_2$-isooctyl | |
| B29 | 2-octyl | —S-tert-dodecyl | |
| B30 | cyclohexyl | —S-tert-dodecyl | |
| 132 | isopropyl | —S(O)-n-dodecyl | 56 |
| 133 | isopropyl | —S(O)-tert-dodecyl | brown resin |
| 134 | isopropyl | —S(O)—CH$_2$CH$_2$—CO$_2$-isooctyl | dark oil |
| 135 | isopropyl | —S(O)—CH$_2$—CO$_2$-isooctyl | dark oil |
| 136 | isopropyl | —S(O)-n-octadecyl | |
| 137 | 1,3-dimethylbutyl | —S(O)-tert-dodecyl | |
| 138 | 1,3-dimethylbutyl | —S(O)-n-dodecyl | |
| 139 | 1,3-dimethylbutyl | —S(O)—CH$_2$CH$_2$—CO$_2$-isooctyl | |
| 140 | 1,3-dimethylbutyl | —S(O)—CH$_2$—CO$_2$-isooctyl | |
| 141 | 2-octyl | —S(O)-tert-dodecyl | |
| 142 | cyclohexyl | —S(O)-tert-dodecyl | |

A mixture of 17.0 g of N-isopropyl-N'-phenyl-p-phenylenediamine, 29.8 g of 3-chlorododecylthiopropane and 0.5 g of potassium iodide in 50 ml of dimethylformamide is stirred for 26 at 115° C. The reaction mixture is cooled to room temperature, diluted with water and extracted with ethyl acetate. The organic phase is washed with water, dried over sodium sulfate and concentrated using a vacuum rotary evaporator. Chromatography of the residue on silica gel using the mobile phase system ethyl acetate/hexane=1:9 yields 15.9 g (45%) of the compound B20 (Table 6), m.p. 56° C., MS (CI): 469 (MH$^{30}$). Oxidation of the compound B20 to form the corresponding sulfoxide compound 132 (Table 6) is carried out in analogy to Example 13, m.p. 56° C., MS (CI): 485 (MH$^{30}$).

In analogy to the procedure described above, using the appropriate phenylenediamine and the appropriate thioether, the compounds B21-B30 and also, as a result of subsequent oxidation using hydrogen peroxide, the compounds 133-142 are obtained (Table 6).

EXAMPLE 16

Preparation of the Compounds B31 and 143

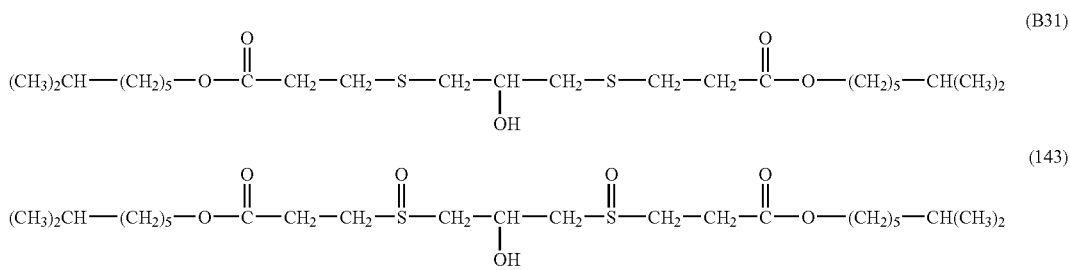

13.7 g of glycidyl-(isooctyloxycarbonylethyl) thioether are added dropwise, over the course of 30 minutes, at 60° C., to 10.9 g of 3-mercaptopropionic acid isooctyl ester and then stirred for a further one hour at 60° C., resulting in the compound B31 in the form of a yellowish oil. MS (CI): 493 (MH$^{30}$).

Oxidation of the compound B31 to form the corresponding disulfoxide compound 143 is carried out in analogy to Example 13, using hydrogen peroxide. MS (CI): 525 (MH$^{30}$).

EXAMPLE 17

Preparation of the Compounds 144-160 (Table 7)

TABLE 7

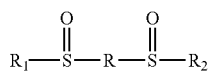

| Compound | R | $R_1$ and $R_2$ | MS (MH$^+$) |
|---|---|---|---|
| 144 | —CH$_2$— | tert-dodecyl | 449 |
| 145 | —CH$_2$— | tert-nonyl | 365 |
| 146 | —CH$_2$— | —CH$_2$—CO$_2$-isooctyl | 453 |
| 147 | —CH$_2$— | —CH$_2$CH$_2$—CO$_2$-isooctyl | 480 |
| 148 | —(CH$_2$)$_2$— | n-octyl | 351 |
| 149 | —(CH$_2$)$_2$— | n-dodecyl | 463 |
| 150 | —((CH$_2$)$_2$— | tert-dodecyl | 463 |
| 151 | —((CH$_2$)$_2$— | tert-nonyl | 379 |
| 152 | —((CH$_2$)$_2$— | —CH$_2$CH$_2$—CO$_2$-isooctyl | 495 |
| 153 | —(CH$_2$)$_3$— | —CH$_2$CH$_2$—CO$_2$-isooctyl | 509 |
| 154 | —(CH$_2$)$_4$— | tert-dodecyl | 491 |
| 155 | —(CH$_2$)$_6$— | tert-dodecyl | 519 |
| 156 | —(CH$_2$)$_6$— | —CH$_2$—CO$_2$-isooctyl | 523 |
| 157 | —(CH$_2$)$_6$— | —CH$_2$CH$_2$—CO$_2$-isooctyl | 551 |
| 158 | —(CH$_2$)$_8$— | tert-dodecyl | 547 |
| 159 | —CH$_2$—C$_6$H$_4$—CH$_2$— | n-dodecyl | 539 |
| 160 | —CH$_2$—C$_6$H$_4$—CH$_2$— | tert-dodecyl | 539 |

General procedure for the preparation of the compounds 144-160 (Table 7): To a appropriate bis-thioether in acetic acid there are added, dropwise, at 50° C., 220 mol % of 35% aqueous hydrogen peroxide solution. Stirring is then carried out for a further 1 to 3 hours at that temperature. In some cases, the product precipitates out from the reaction solution directly; otherwise, extraction with ethyl acetate is carried out and working-up is carried out in customary manner.

EXAMPLE 18

Preparation of the Compounds B32, B33, 161 and 162 (Table 8)

TABLE 8

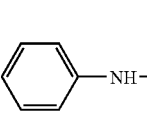

| Compound | R | MS (MH$^+$) |
|---|---|---|
| B32 | —S-n-dodecyl | 513 |
| B33 | —S-tert-dodecyl | 513 |
| 161 | —S(O)-n-dodecyl | 529 |
| 162 | —S(O)-tert-dodecyl | 529 |

A mixture of 15.4 g of N-isopropyl-N'-phenyl-p-phenylenediamine, 25 g of bromoacetic acid 2-n-dodecylthioethyl ester and 47 g of potassium carbonate in 50 ml of dimethylformamide is stirred for 8 hours at 80° C. Chromatography of the reaction mixture on silica gel using the mobile phase system hexane/ethyl acetate=1:1 yields 26.4 g (75%) of the compound B32 (Table 8), m.p. 51° C., MS (CI): 513 (MH$^{30}$).

To a solution of 13.2 g of the compound B32 (Table 8) in 150 ml of acetone there are added 5 g of 35% aqueous hydrogen peroxide solution and stirring is carried out for 8.5 hours at 45° C. Water is then added to the reaction mixture. The product is extracted with ethyl acetate. After customary working-up, 12.5 g (92%) of the compound 161, viscous oil, are obtained. MS(Cl): 529 (MH$^{3o}$).

In analogy to the procedure described above, using bromoacetic acid 2-tert-dodecylthioethyl ester instead of bromoacetic acid 2-n-dodecylthioethyl ester, the compound B33 and also, as a result of subsequent oxidation using hydrogen peroxide, the compound 162 are obtained (Table 8).

EXAMPLE 19

Preparation of the Compounds B34, B35, B36, 163, 164 and 165 (Table 9)

TABLE 9

$$R_7O-\underset{\underset{OR_8}{|}}{\overset{\overset{OR_6}{|}}{Si}}-R$$

| Compound | $R_6$, $R_7$ and $R_8$ | R | MS (MH$^+$) |
| --- | --- | --- | --- |
| B34 | methyl | —CH$_2$CH$_2$CH$_2$—S-n-octyl | 308 |
| B35 | ethyl | —CH$_2$CH$_2$CH$_2$—S-n-octyl | 350 |
| B36 | methyl | —CH$_2$CH$_2$CH$_2$—S-tert-dodecyl | 365 |
| 163 | methyl | —CH$_2$CH$_2$CH$_2$—S(O)-n-octyl | 324 |
| 164 | ethyl | —CH$_2$CH$_2$CH$_2$—S(O)-n-octyl | 366 |
| 165 | methyl | —CH$_2$CH$_2$CH$_2$—S(O)-tert-dodecyl | 381 |

To a suspension of 2.47 g of sodium hydride in 20 ml of hexane there are added, dropwise, at 0-25° C., g of n-octanethiol. After the evolution of hydrogen is complete, 15 g of 3-bromopropyl-trimethoxysilane in 20 ml of hexane are added. The white suspension is stirred for 10 hours at 70° C. The reaction mixture is cooled to room temperature and filtered, and the filtrate is concentrated using a vacuum rotary evaporator. Distillation of the residue in a Kugelrohr oven (b.p. 110° C./0.1 mbar) yields 15.6 g (66%) of the compound B34 (Table 9), colourless liquid, MS (Cl): 308 (MH$^{3o}$).

In analogous manner, the compound B35 (Table 9) is obtained using 3-bromopropyltriethoxysilane instead of 3-bromopropyl-trimethoxysilane. MS (Cl): 350 (MH$^{3o}$).

Likewise, in analogous manner, the compound B36 (Table 9) is obtained using tert-dodecylmercaptan instead of n-octanethiol. MS (Cl): 365 (MH$^{3o}$).

Oxidation of the compounds B34, B35 and B36 to form the corresponding sulfoxide compound 163, 164 and 165 is carried out in analogy to Example 13, using hydrogen peroxide. The molecular weights measured are given in Table 9.

EXAMPLE 20

Preparation of the Compounds B37-B41 and 166-170 (Table 10)

TABLE 10

| Compound | R | MS (MH$^+$) |
| --- | --- | --- |
| B37 | —S-n-dodecyl | 600 |
| B38 | —S—CH$_2$CH$_2$—CO$_2$-isooctyl | 615 |
| B39 | —S-tert-dodecyl | 599 |
| B40 | —S-n-octadecyl | 671 |
| B41 | —S-n-octyl | 552 |
| 166 | —S(O)-n-dodecyl | 616 |
| 167 | —S(O)-CH$_2$CH$_2$—CO$_2$-isooctyl | 631 |
| 168 | —S(O)-tert-dodecyl | 615 |
| 169 | —S(O)-n-octadecyl | 687 |
| 170 | —S(O)-n-octyl | 568 | a) Preparation of the Epoxide of Formula A4

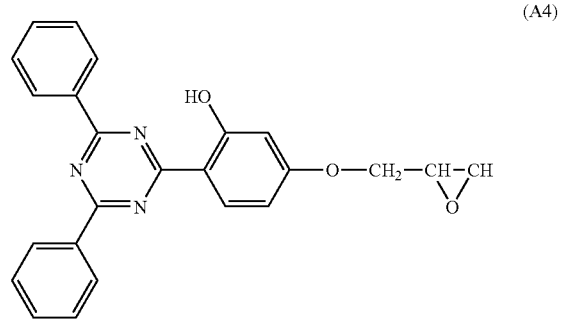

To a suspension of 200 g of 2,4-diphenyl-6-(2,4-dihydroxyphenyl)-1,3,5-triazine and 138 g of anhydrous potassium carbonate in 2 liters of toluene there are added, at 80° C., 176.6 g of epibromohydrin. The reaction mixture is stirred for a further 14 hours at that temperature, then filtered whilst and subsequently cooled. The precipitated product is filtered off and dried in a dying cabinet, resulting in 123 g (53%) of the epoxide of formula A4, light-yellow power, m.p. 186° C., MS (Cl): 398 (MH$^{3o}$).

b) Preparation of the sulfides B37-B41 (Table 10).

A solution of 9.95 g of the epoxide of formula A4 [prepared in accordance with Example 20a] and 6.1 g of n-dodecylmercaptan in 10 ml of dimethylformamide is stirred at 110° C. for 44 hours. The reaction mixture is cooled and diluted with water; the precipitated product is filtered off the residue is dried, resulting in 14.2 g (95%) of the compound B37 (Table 10), yellow powder, m.p. 80° C., MS (Cl): 600 (MH$^{3o}$).

In analogy to Example 20b, the compounds B38-B41 (Table 10) are obtained using 2-isooctyloxycarbonylethylmercaptan, tert-dodecylmercaptan, n-octadecylmercaptan and n-octylmercaptan instead of n-dodecylmercaptan.

c) Preparation of the sulfoxides 166-170 (Table 10).

To a suspension of 4 g of the compound B37 [prepared in accordance with Example 20c] in 10 ml of glacial acetic acid there is added, at 45° C., 0.45 g of 35% aqueous hydrogen peroxide solution. The reaction mixture is then stirred for a further 7 hours at that temperature. After adding water, the product precipitates out. The precipitate is filtered off, washed with water and then dried in a drying cabinet, resulting in 3.0 g (76%) of the compound 166 (Table 10), yellow powder, m.p. 99° C., MS (CI): 616 (MH$^{30}$).

In analogous manner, the compounds B38-B41 are oxidised to form the sulfoxides 167-170 (Table 10).

EXAMPLE 21

Preparation of the Compounds B42-B45 and 171-174 (Table 11)

TABLE 11

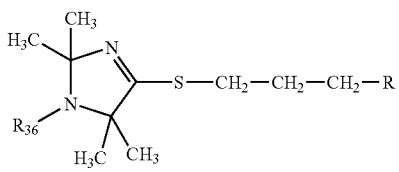

| Compound | R$_{36}$ | R | MS (MH$^+$) |
|---|---|---|---|
| B42 | H | —S-tert-dodecyl | 401 |
| B43 | H | —S-n-dodecyl | 401 |
| B44 | methyl | —S-tert-dodecyl | 415 |
| B45 | methyl | —S-n-dodecyl | 415 |
| 171 | H | —S(O)-tert-dodecyl | 417 |
| 172 | H | —S(O)-n-dodecyl | 417 |
| 173 | methyl | —S(O)-tert-dodecyl | 431 |
| 174 | methyl | —S(O)-n-dodecyl | 431 | a) Preparation of the Compounds B42 and B43 (Table 11).

A solution of 27.9 g of 3-chloropropyl-tert-dodecyl thioether [prepared in analogy to U.S. Pat. No. 3,038,944; Example IV] and 15.8 g of 2,2,5,5-tetramethyl-2,5-dihydro-3H-imidazole-4-thione in 50 ml of toluene is stirred for 24 hours at 120° C. The reaction mixture is cooled, 50 ml of water containing 4 g of sodium hydroxide are added and extraction with ethyl acetate is carried out. The organic phase is washed with water, dried over sodium sulfate and concentrated using a vacuum rotary evaporator. Distillation of the residue in a Kugelrohr oven (b.p. 130° C./0.02 bar) yields 24.5 g (63%) of the compound B42 (Table 11), yellow oil, MS (CI): 401 (MH$^{30}$).

In analogy to Example 21a, using 3-chloropropyl-n-dodecyl thioether instead of 3-chloropropyl-tert-dodecyl thioether, the compound B43 (Table 11), yellow oil, MS (CI): 401 (MH$^{30}$), is obtained.

b) Preparation of the Compounds B44 and B45 (Table 11).

A mixture of 7.93 g of the compound B42 [prepared in accordance with Example 21a], 0.7 g of paraformaldehyde and 1 g of formic acid in 12 ml of toluene and 3 ml of water is maintained at 75° C. for one hour. The reaction mixture is concentrated using a vacuum rotary evaporator. The residue is made alkaline using dilute sodium hydroxide solution and extracted with toluene. The organic phase is washed with water, dried over sodium sulfate and concentrated using the vacuum rotary evaporator, resulting in 7.9 g (96%) of the compound B44 (Table 11), reddish oil, MS (CI): 415 (MH$^{30}$).

In analogy to Example 21b, using the compound B43 [prepared in accordance with Example 21a] the compound B45 (Table 11), yield 82%, orange oil, MS (CI): 415 (MH$^{30}$), is obtained.

c) Preparation of the Sulfoxides 171-174 (Table 11).

Oxidation of the compounds B42-B45 to form the corresponding sulfoxide compounds 171 to 174 is carried out in analogy to Example 13, using hydrogen peroxide. The molecular weights measured are given in Table 11.

EXAMPLE 22

Grafting of Polybutadiene

The grafting agents according to the invention which are listed in Table 12 are added to a polybutadiene [low-cis BR BUNA CB 529 T (RTM) from Bayer] pre-stabilised using 0.2% Irganox 1520 (RTM) [4,6-bis(octylthiomethyl)-2-methylphenol]. The actual grafting is accomplished by kneading the rubber in a Brabender Plasticorder at 160° C. and 40 revolutions per minute for 15 minutes. The rubber is then press-moulded in a heated press at 90° C. for 10 minutes to form 2 mm-thick plates. The plates are extracted with acetone at room temperature for 3 days in a Soxhlet apparatus. The rates of incorporation of the grafting agents into the rubber are determined by means of sulfur determination and $^1$H-NMR (CDCl$_3$). The results are compiled in Table 12.

TABLE 12

| Example | Grafting agent | Sulfur incorporation in % by weight | Antioxidant incorporation in % by weight |
|---|---|---|---|
| 22a$^{a)}$ | — | — | — |
| 22b$^{a)}$ | 1% Irganox 1076 (RTM)$^{c)}$ | — | — |
| 22c$^{b)}$ | 1% compound 101 | 48 | 50 |
| 22d$^{b)}$ | 1% compound 102 | 38 | 50 |
| 22e$^{b)}$ | 1% compound 112 | 50 | |
| 22f$^{b)}$ | 1% compound 113 | 26 | |
| 22g$^{b)}$ | 1% compound 121 | 33 | |
| 22h$^{b)}$ | 1% compound 122 | 47 | |
| 22i$^{b)}$ | 1% compound 124 | 46 | |
| 22j$^{b)}$ | 1% compound 126 | | 52 |
| 22k$^{b)}$ | 1% compound 134 | | 42 |
| 22l$^{b)}$ | 1% compound 162 | | 48 |

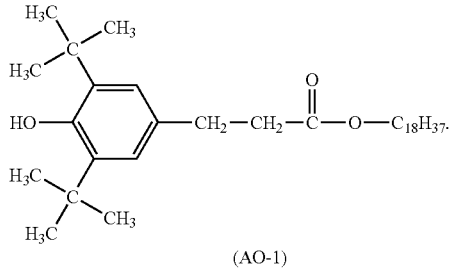

(AO-1)

$^{a)}$Comparison Example.
$^{b)}$Example according to the invention.
$^{c)}$Irganox 1076 (RTM) [Ciba Spezialitätenchemie AG] is a compound of formula AO-1

The Comparison Example 22a clearly shows that the basic stabiliser, Irganox 1520 (RTM), which likewise contains sulfur, does not graft and is completely extracted from the rubber with acetone.

The thermo-oxidative stability of the rubber plates, after extraction with acetone, is determined by means of a) oven ageing, b) ageing in silicone oil and c) DSC measurement. The oven ageing is carried out at 70° C. in toluene, the formation of gel being measured as a function of time. The longer it takes for the gel to form, the better the rubber is stabilised. The ageing in silicone oil is carried out at 140° C. for 30 minutes. The gel content is then measured in % by weight. In the case of the DSC measurement, the time in minutes until the appearance of the exotherm peak is measured. The longer the time, the more stable the rubber. The results are compiled in Table 13.

TABLE 13

| Example | Oven ageing, in % by weight of gel, after no. of days | | | Ageing in silicone oil, in % by weight of gel | DSC 160° C. minutes until peak |
|---|---|---|---|---|---|
| | 1 | 2 | 6 | | |
| 22b[a] | 81 | | | 94 | 1.8 |
| 22c[b] | 0.2 | 0.2 | 43 | 0.17 | 17.5 |
| 22d[b] | 0.3 | 0.3 | 6 | 0.24 | 12.6 |
| 22h[b] | | | | 0.70 | |
| 22i[b] | | | | 0.20 | | a) For footnotes [a], [b] and [c], see the end of Table 12.

The results in Tables 12 and 13 clearly show that the grafting agents according to the invention not only are analytically demonstrated to be stable to extraction but also exert a marked antioxidative action in the grafted state.

EXAMPLE 23

Vulcanisation of Polybutadiene

The grafting agents (vulcanisation agents) under test are incorporated into the rubber [low-cis BR BUNA CB 529 T (RTM) from Bayer] in a concentration of 2% by weight at 60° C. in a mixing roll mill. Using those specimens, in an oscillation rheometer at 180° C., the change in torque occurring at the oscillator and the loss modulus tan δ as a function of time are measured. An increase in torque and a decrease in tan δ indicates an increase in cross-linking and a change from the plastic to the elastic state, respectively. In addition, the intrinsic viscosity is determined at 25° C. in toluene. There is a direct relationship between the intrinsic viscosity and the molecular weight. An increase in intrinsic viscosity indicates an increase in molecular weight and, consequently, cross-linking. The results are compiled in Table 14.

TABLE 14

| Example | Grafting agent (vulcanisation agent) | Torque (dNm) | tan δ | Intrinsic viscosity (mg/g) |
|---|---|---|---|---|
| 23a[a] | — | 1.1 | 0.96 | 219 |
| 23b[b] | 2% compound 108 | 1.8 | 0.65 | 256 |
| 23c[b] | 2% compound 109 | 1.3 | 0.80 | 248 |

[a] Comparison Example.
[b] Example according to the invention.

The results in Table 14 show that the grafting agents (vulcanisation agents) in accordance with the invention initiate cross-linking under the conditions described.

EXAMPLE 24

Cross-linking of Polybutadiene

The grafting agent (vulcanisation agent) 152 (Table 7) under test is incorporated into the rubber [low-cis BR BUNA CB 529 T (RTM) from Bayer] in a concentration of 3% by weight at 60° C. in a mixing roll mill. After mixing-in, the gel content, measured in toluene at room temperature, is 0.20%. When the polybutadiene sample is maintained at 200° C. for 15 minutes, the gel content rises to 74%. That pronounced rise in the gel content is a consequence of the chemical cross-linking caused by the compound 152 (Table 7).

What is claimed is:

1. A compound of formula I

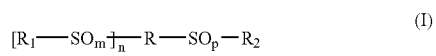

wherein, when n is 0,

R is

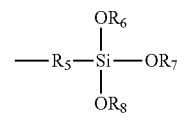

or a radical of formula III, IV, V, VI, VIII or IX

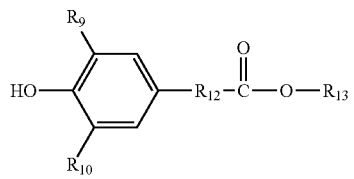

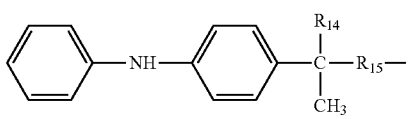

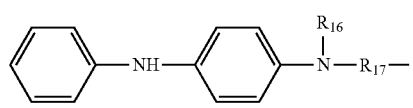

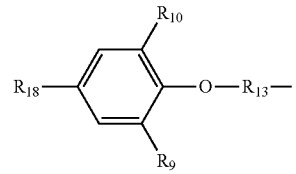

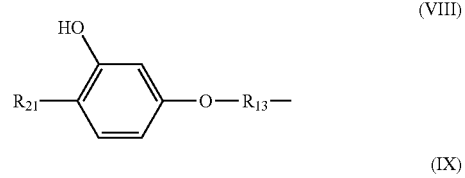

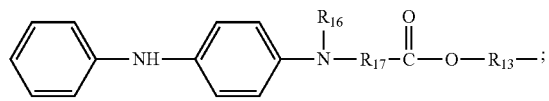

when n is 1,
R is

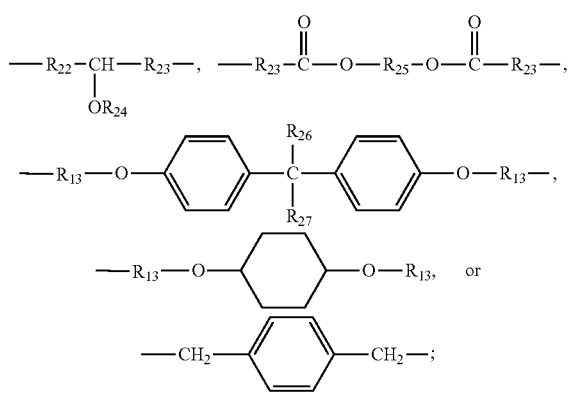

when n is 2,
R is

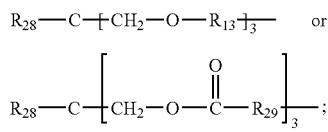

when n is 3,
R is

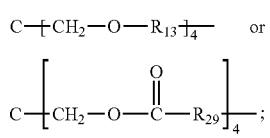

$R_1$ is $C_1$-$C_{25}$alkyl,

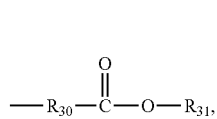 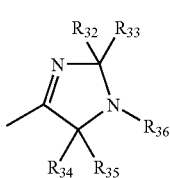

or $C_2$-$C_{18}$hydroxyalkyl,
$R_2$ is $C_1$-$C_{25}$alkyl,

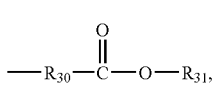 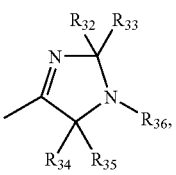

$C_2$-$C_{18}$hydroxyalkyl or a radical of formula III or IX,
$R_5$ is $C_1$-$C_{12}$alkylene, or $C_2$-$C_{12}$alkylene interrupted by oxygen, $R_6$, $R_7$ and $R_8$ are each independently of the others hydrogen, $C_1$-$C_{12}$alkyl, $C_2$-$C_{12}$alkyl interrupted by oxygen or by sulfur; or $C_3$-$C_{12}$alkenyl, $R_9$ is hydrogen, $C_1$-$C_8$alkyl, $C_5$-$C_8$cycloalkyl, $C_7$-$C_9$phenylalkyl or phenyl, $R_{10}$ is $C_1$-$C_8$alkyl, $C_5$-$C_8$cycloalkyl, $C_7$-$C_9$phenylalkyl, phenyl,

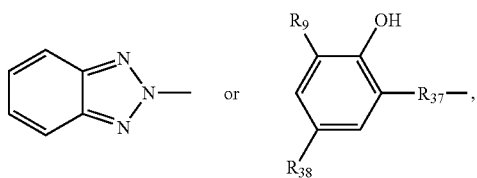

$R_{12}$ is a direct bond or unsubstituted or $C_1$-$C_4$alkyl-substituted $C_1$-$C_8$alkylene, $R_{13}$ is $C_1$-$C_8$alkylene or

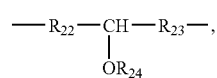

$R_{14}$ is hydrogen or $C_1$-$C_4$alkyl,
$R_{15}$ is $C_1$-$C_4$alkylene,
$R_{16}$ is hydrogen, cyclohexyl or $C_3$-$C_{12}$alkyl,
$R_{17}$ is $C_1$-$C_8$alkylene or

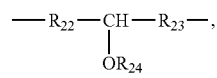

$R_{18}$ is hydrogen or $C_1$-$C_{12}$alkyl,
$R_{21}$ is

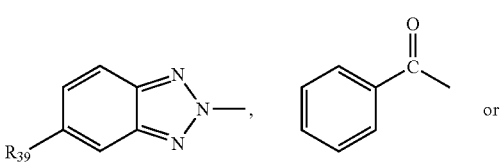

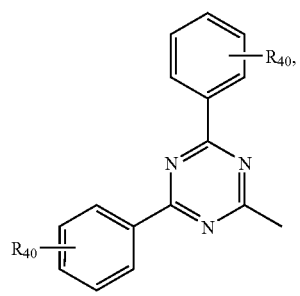

$R_{22}$ is a direct bond or $C_1$-$C_8$alkylene,
$R_{23}$ is $C_1$-$C_8$alkylene,
$R_{24}$ is $C_1$-$C_{25}$alkyl, $C_2$-$C_{25}$alkanoyl,

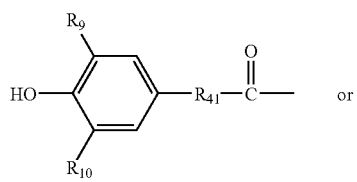

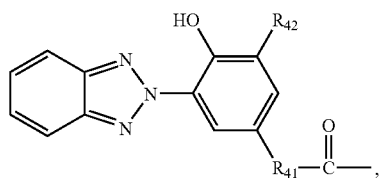

$R_{25}$ is $C_2$-$C_{18}$alkylene or $C_2$-$C_{18}$alkylene interrupted by oxygen or by sulfur, $R_{26}$ and $R_{27}$ are each independently of the other hydrogen, $CF_3$, $C_1$-$C_{12}$alkyl or phenyl, or $R_{26}$ and $R_{27}$, together with the carbon atom to which they are bonded, form a $C_5$-$C_8$cycloalkylidene ring that is unsubstituted or substituted by from 1 to 3 $C_1$-$C_4$alkyl groups, $R_{28}$ is $C_1$-$C_8$alkyl, $R_{29}$ is $C_1$-$C_{12}$alkylene, $R_{30}$ is $C_1$-$C_8$alkylene, $R_{31}$ is $C_1$-$C_{25}$alkyl, $R_{32}$, $R_{33}$, $R_{34}$ and $R_{35}$ are each independently of the others $C_1$-$C_8$alkyl; or the radicals $R_{32}$ and $R_{33}$ or the radicals $R_{34}$ and $R_{35}$, together with the carbon atom to which they are bonded, form a $C_5$-$C_u$cycloalkylidene ring, $R_{36}$ is hydrogen, $C_1$-$C_{18}$alkyl, $C_3$-$C_6$alkenyl, $C_3$-$C_6$alkynyl, $C_7$-$C_{12}$phenylalkyl, $C_1$-$C_8$acyl, $C_1$-$C_{18}$alkoxy, $C_1$-$C_{18}$hydroxyalkoxy, $C_2$-$C_1$olkenyloxy or $C_5$-$C_{12}$cycloalkoxy, $R_{37}$ is $C_1$-$C_4$alkylene, sulfur or $C_2$-$C_8$alkylidene, $R_{38}$ is hydrogen, $C_1$-$C_o$lkyl, $C_5$-$C_8$cycloalkyl or phenyl, $R_{39}$ is hydrogen, halogen, —SO—$C_1$-$C_{25}$alkyl or —$SO_2$—$C_1$-$C_{25}$alkyl, $R_{40}$ is hydrogen, $C_1$-$C_8$alkyl or phenyl, $R_{41}$ is a direct bond, or unsubstituted or $C_1$-$C_4$alkyl-substituted $C_1$-$C_8$alkylene, $R_{42}$ is hydrogen, $C_1$-$C_8$alkyl, $C_5$-$C_8$cycloalkyl or $C_7$-$C_9$phenylalkyl, m is 0, 1 or 2, n is 0, 1, 2 or 3, and p is 1 or 2;

with the proviso that, when n is 0, R is a radical of formula V, $R_{17}$ is

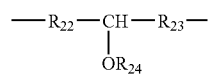

and $R_{22}$ and $R_{23}$ are methylene, then $R_{24}$ is other than hydrogen.

2. A compound according to claim 1, wherein, when n is 0,

R is

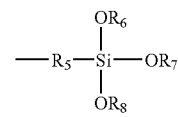

or a radical of formula III, IV, V, VI, VIII or IX;

when n is 1,

R is

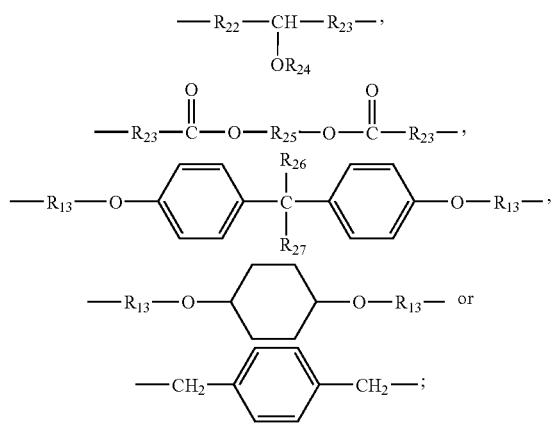

when n is 2,

R is

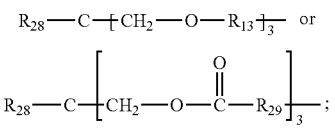

when n is 3,

R is

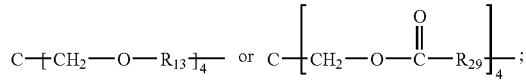

$R_1$ is $C_4$-$C_{18}$alkyl,

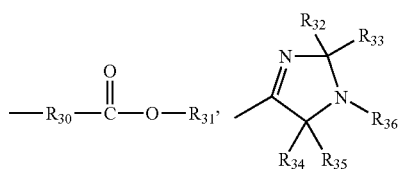

$R_2$ is $C_4$-$C_{18}$alkyl,

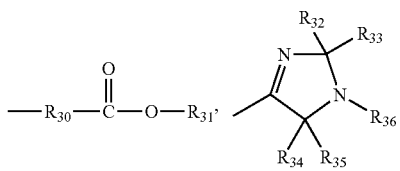

$C_2$-$C_8$hydroxyalkyl or a radical of formula III or IX,
$R_5$ is $C_1$-$C_8$alkylene,
$R_6$, $R_7$ and $R_8$ are each independently of the others hydrogen, $C_1$-$C_8$alkyl or $C_3$-$C_8$alkenyl,
$R_9$ is $C_1$-$C_5$alkyl, cyclohexyl or $C_7$-$C_9$phenylalkyl,
$R_{10}$ is $C_1$-$C_8$alkyl, cyclohexyl, $C_7$-$C_9$phenylalkyl,

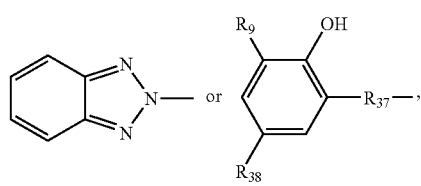

$R_{12}$ is $C_1$-$C_8$alkylene;
$R_{13}$ is $C_1$-$C_8$alkylene or

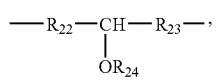

$R_{14}$ is $C_1$-$C_4$alkyl,
$R_{15}$ is $C_1$-$C_4$alkylene,
$R_{16}$ is $C_3$-$C_8$alkyl,
$R_{17}$ is $C_1$-$C_8$alkylene or

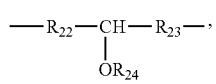

$R_{18}$ is hydrogen or $C_1$-$C_8$alkyl,
$R_{21}$ is

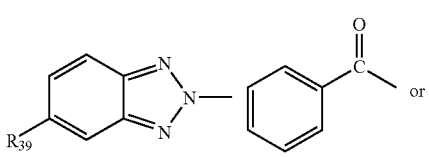

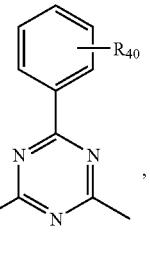

$R_{22}$ is $C_1$-$C_6$alkylene,
$R_{23}$ is $C_1$-$C_6$alkylene,
$R_{24}$ is $C_1$-$C_{12}$alkyl, $C_2$-$C_{12}$alkanoyl,

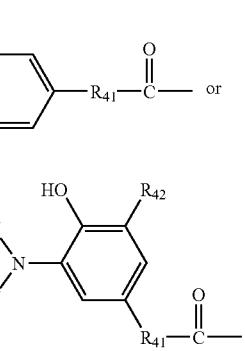

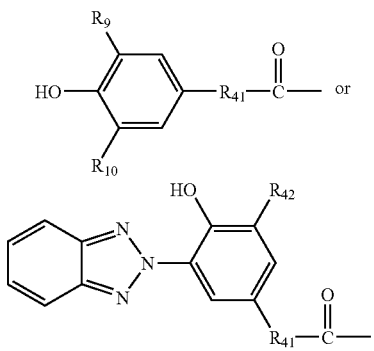

$R_{25}$ is $C_2$-$C_8$alkylene,
$R_{26}$ and $R_{27}$ are each independently of the other hydrogen or $C_1$-$C_4$alkyl, or $R_{26}$ and $R_{27}$, together with the carbon atom to which they are bonded, form a cyclohexylidene ring,
$R_{28}$ is $C_1$-$C_4$alkyl
$R_{29}$ is $C_1$-$C_4$alkylene,
$R_{30}$ is $C_1$-$C_4$alkylene,
$R_{31}$ is $C_4$-$C_{18}$alkyl,
$R_{32}$, $R_{33}$, $R_{34}$ and $R_{35}$ are each independently of the others $C_1$-$C_4$alkyl; or the radicals $R_{32}$ and $R_{33}$ or the radicals $R_{34}$ and $R_{35}$, together with the carbon atom to which they are bonded, form a cyclohexylidene ring,
$R_{36}$ is hydrogen, $C_1$-$C_8$alkyl, benzyl, $C_1$-$C_3$acyl, $C_1$-$C_8$alkoxy, $C_2$-$C_8$hydroxyalkoxy, $C_3$-$C_8$alkenyloxy or cyclohexyloxy,
$R_{37}$ is $C_1$-$C_4$alkylene or $C_2$-$C_4$alkylidene,
$R_{38}$ is hydrogen, $C_1$-$C_4$alkyl or cyclohexyl,
$R_{39}$ is hydrogen, chlorine, —SO—$C_1$-$C_{12}$alkyl or —$SO_2$—$C_1$-$C_{12}$alkyl,
$R_{40}$ is hydrogen or $C_1$-$C_4$alkyl,
$R_{41}$ is $C_1$-$C_8$alkylene,
$R_{42}$ is $C_1$-$C_8$alkyl, cyclohexyl or $C_7$-$C_9$phenylalkyl,
m is 0, 1 or 2,
n is 0, 1, 2 or 3, and
p is 1 or 2.

* * * * *